(12) United States Patent
Kersten et al.

(10) Patent No.: US 7,823,306 B1
(45) Date of Patent: Nov. 2, 2010

(54) ROOM FOR CONDUCTING MEDICAL PROCEDURES

(75) Inventors: John D. Kersten, Port Jefferson Station, NY (US); Alex Darian, Port Jefferson Station, NY (US); Raymond V. Damadian, Woodbury, NY (US)

(73) Assignee: Fonar Corporation, Melville, NY (US)

( * ) Notice: Subject to any disclaimer, the term of this patent is extended or adjusted under 35 U.S.C. 154(b) by 887 days.

(21) Appl. No.: 09/919,286

(22) Filed: Jul. 31, 2001

Related U.S. Application Data

(60) Provisional application No. 60/222,080, filed on Aug. 1, 2000.

(51) Int. Cl.
*G09F 19/00* (2006.01)

(52) U.S. Cl. .............................. 40/436; 40/471; 40/438; 40/518

(58) Field of Classification Search ................. 600/409, 600/418, 427; 348/53, 77; 40/471, 518, 40/436, 438; 446/149–152
See application file for complete search history.

(56) References Cited

U.S. PATENT DOCUMENTS

| | | | |
|---|---|---|---|
| 1,196,136 A * | 8/1916 | Morrone | 40/370 |
| 2,377,553 A * | 6/1945 | Heck et al. | 160/24 |
| 2,419,802 A | 4/1947 | Horne | |
| 2,952,931 A | 9/1960 | Manduca | |
| 4,173,087 A * | 11/1979 | Saylor et al. | 40/518 |
| 4,651,099 A * | 3/1987 | Vinegar et al. | 324/320 |
| 4,707,663 A | 11/1987 | Minkoff et al. | |
| 4,763,428 A | 8/1988 | Fischer | |
| 4,804,261 A | 2/1989 | Kirschen | |
| 5,076,275 A | 12/1991 | Bechor et al. | |
| 5,112,294 A | 5/1992 | Syers | |
| 5,134,373 A | 7/1992 | Tsuruno et al. | |
| 5,277,184 A | 1/1994 | Messana | |
| 5,304,112 A | 4/1994 | Mrklas et al. | |
| 5,355,885 A | 10/1994 | Tsuda et al. | |
| 5,493,802 A * | 2/1996 | Simson | 40/471 |
| D373,584 S | 9/1996 | Anand | |

(Continued)

*Primary Examiner*—Long V Le
*Assistant Examiner*—Sanjay Cattungal
(74) *Attorney, Agent, or Firm*—Brandon N. Sklar, Esq.; Kaye Scholer LLP

(57) ABSTRACT

A room for use in conducting medical procedures includes an image on a screen disposed in the room. The room preferably includes a track for disposing the screen across the room to create a panoramic view of the scene in the screen. Preferably the track, and hence the image on the screen disposed on the track, are arcuate. The screen provides a virtual reality and a calming effect to the patient undergoing the procedure. The screen can be moved mechanically around the room to display different images on the screen. The screen can be changed to provide a different set of images. Ceiling lights, sounds and smells can be added to the room to further accent the theme of the screen's image and enhance the overall calming effect by portraying the medical procedure room as the scene in the screen. Illumination may be provided behind the screen, as well. The medical procedure may be a magnetic resonance imaging procedure, in which case the room comprises a magnetic resonance imaging assembly. The magnetic resonance imaging assembly may be an open magnetic resonance imaging assembly. The assembly may define, at least in part, the room. Methods of preparing a room for a medical procedure and methods of conducting a magnetic resonance imaging procedure are also disclosed.

57 Claims, 16 Drawing Sheets

U.S. PATENT DOCUMENTS

| | | | | |
|---|---|---|---|---|
| 5,627,902 | A | 5/1997 | Ziarati | |
| 5,676,633 | A | 10/1997 | August | |
| 5,681,259 | A * | 10/1997 | August | 600/27 |
| 5,842,987 | A * | 12/1998 | Sahadevan | 600/407 |
| 5,864,331 | A | 1/1999 | Anand et al. | |
| 5,877,732 | A | 3/1999 | Ziarati | |
| 5,917,395 | A * | 6/1999 | Overweg | 335/296 |
| 5,924,646 | A * | 7/1999 | Pouya | 242/538.1 |
| 5,944,574 | A * | 8/1999 | Small et al. | 446/149 |
| 5,953,840 | A * | 9/1999 | Simson et al. | 40/471 |
| 6,023,165 | A | 2/2000 | Damadian et al. | |
| 6,075,364 | A | 6/2000 | Damadian et al. | |
| 6,198,285 | B1 * | 3/2001 | Kormos et al. | 324/318 |
| 6,201,394 | B1 | 3/2001 | Danby et al. | |
| 6,208,145 | B1 | 3/2001 | Danby et al. | |
| 6,335,623 | B1 * | 1/2002 | Damadian et al. | 324/320 |
| 6,414,490 | B1 | 7/2002 | Damadian et al. | |
| 6,503,188 | B1 * | 1/2003 | August | 600/27 |
| 2002/0109794 | A1 * | 8/2002 | Bergman | 348/841 |

* cited by examiner

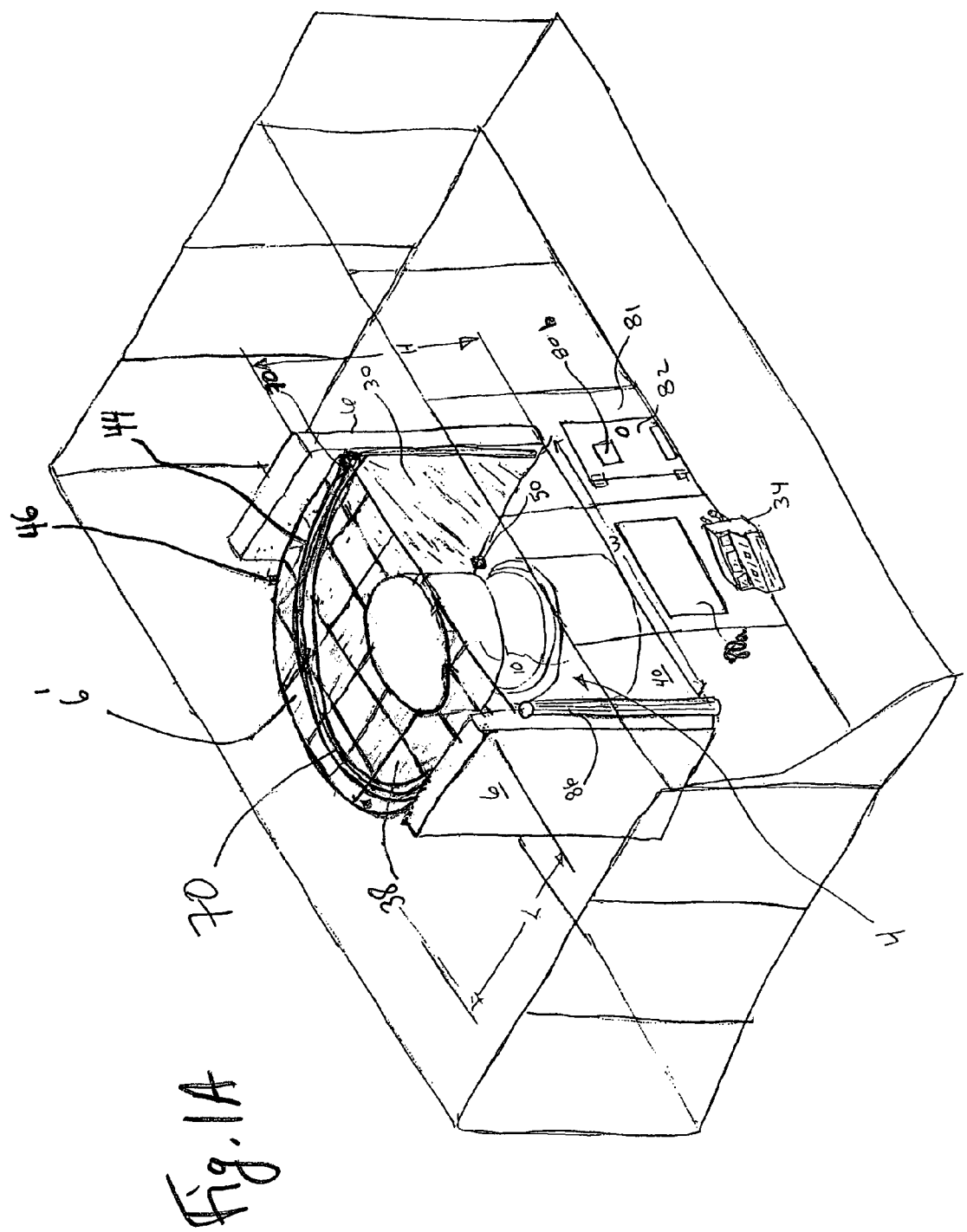

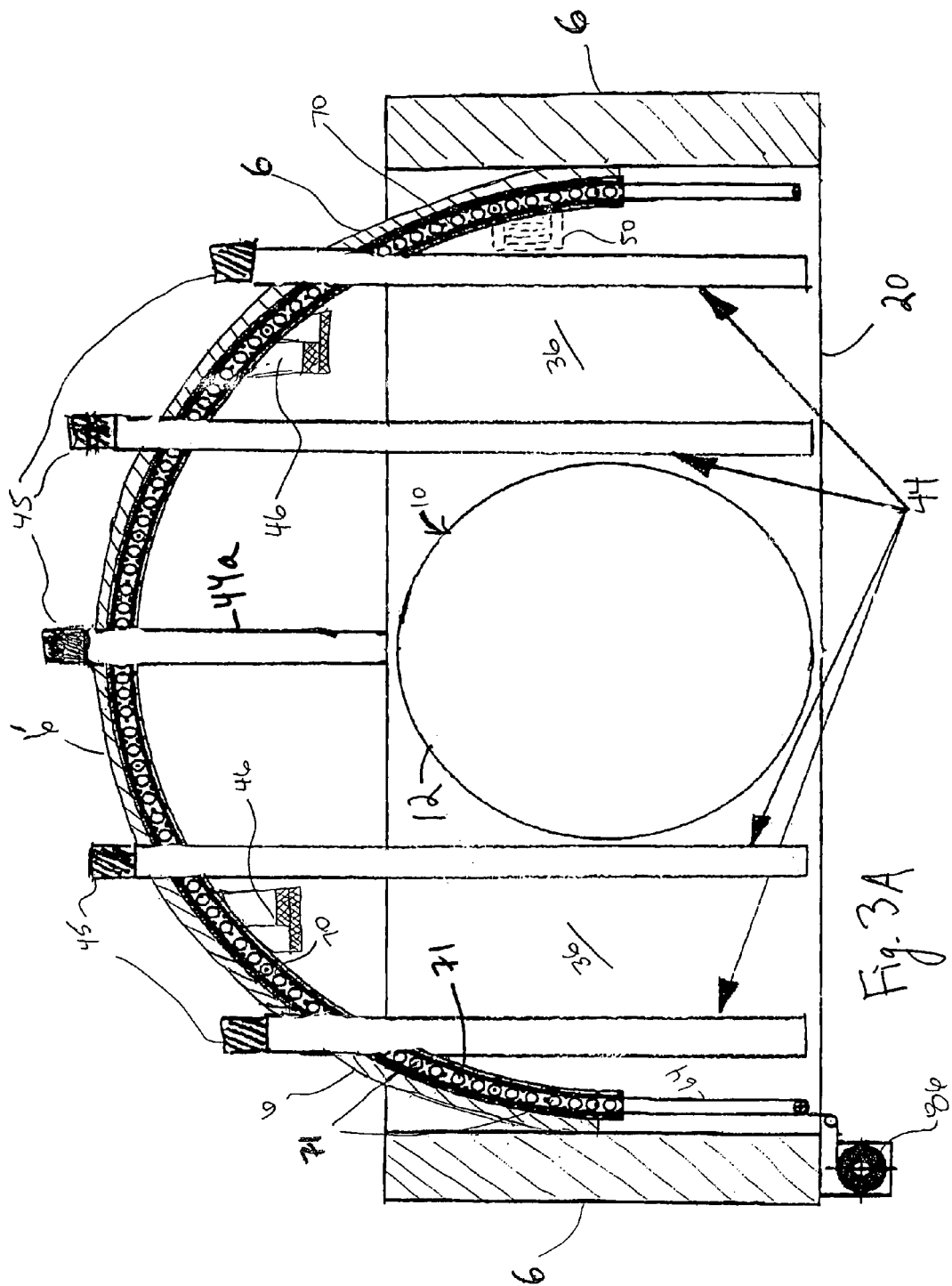

ROOM FOR CONDUCTING MEDICAL PROCEDURES

BENEFIT OF PROVISIONAL APPLICATION

The present application claims the priority of U.S. Ser. No. 60/222,080, filed on Aug. 1, 2000, assigned to the assignee of the present invention and incorporated by reference herein, in its entirety.

FIELD OF THE INVENTION

This invention generally relates to a room for conducting medical procedures, such as a room for conducting magnetic resonance imaging, where the room comprises an apparatus that imparts calmness to the patient during the medical procedure.

BACKGROUND OF THE INVENTION

Magnetic resonance imaging ("MRI") is a well known, highly useful technique for diagnosing abnormalities in biological tissue. MRI can detect abnormalities which are difficult or impossible to detect by other techniques, without the use of x-rays or invasive procedures.

MRI uses changes in the angular momentum or spin of the atomic nuclei of certain elements within body tissue in a static magnetic field after excitation by radio frequency energy, to derive images containing useful information concerning the condition of the tissue. During an MRI procedure, the patient is inserted into an imaging volume of a primary field magnet. The vector of the angular momentum or spin of nuclei containing an odd number of protons or neutrons tends to align with the direction of the static magnetic field generated in the imaging volume by the magnet. A transmitting antenna proximate to the imaging volume emits a pulse or pulses of radio frequency energy. The radio frequency energy has a particular bandwidth of frequency, referred to as the resonant or Larmor frequency, that shifts the vectors of the nuclei out of alignment with the applied magnetic field. The spins of the nuclei then turn or "precess" around the direction of the applied primary magnetic field. As their spins precess, the nuclei emit small radio frequency signals, referred to as magnetic resonance ("MR") signals, at the resonant or Larmor frequency, which are detected by a radio frequency receiving antenna tuned to that frequency. The receiving antenna is typically positioned within the imaging volume proximate the patient. Gradient magnetic fields are provided to spatially encode the MR signals emitted by the nuclei. After the cessation of the application of radio frequency waves, the precessing spins gradually drift out of phase with one another, back into alignment with the direction of the applied magnetic field. This causes the MR signals emitted by the nuclei to decay.

The same antenna may act as the transmitting and receiving antenna. The MR signals detected by the receiving antenna are amplified, digitized and processed by the MRI system. Hydrogen, nitrogen, phosphorous, carbon and sodium are typical nuclei detected by MRI. Hydrogen is most commonly detected because it is the most abundant nuclei in the human body and emits the strongest MR signal.

The rate of decay of the MR signals varies for different types of tissue, including injured or diseased tissue, such as cancerous tissue. By correlating the gradient magnetic fields and the particular frequency of the radio frequency waves applied at various times with the rate of decay of the MR signals emitted by the patient by known mathematical techniques, it is possible to determine the concentrations and the condition of the environment of the nuclei of interest at various locations within the patient's body. This information is typically displayed as an image with varying intensities, which are a function of the concentration and environment of the nuclei of interest.

Patients need to lie very still for an extended period of time during an MRI scanning procedure. One type of magnet assembly for performing magnetic resonance imaging on a patient requires that the patient be positioned in a narrow, substantially enclosed gap region within a series of circular superconducting coils spaced along an axis. The walls of the gap may be very close to the patient and may cause claustrophobic reactions in the patient. Certain obese or pregnant patients cannot fit within the gap. In addition, these magnet assemblies may prevent another person, such as a medical attendant or physician, from having easy access to the patient while the patient is within the MRI assembly. Adding to these problems is the significant noise from movement of the magnets that may be generated during the operation of the MRI system. This noise can cause further stress for the patient. It is difficult for those patients who are uncomfortable within the narrow, noisy, claustrophobic gap region to lie still enough for accurate MRI images to be developed. Sedation is often required.

"Open" type MRI assemblies have been developed which have large gap regions for receiving a patient. Open MRI assemblies are described in U.S. Pat. No. 6,201,394 B1, issued Mar. 13, 2001, U.S. Pat. No. 6,023,165, issued Feb. 8, 2000 and U.S. Pat. No. 6,414,490 B1, issued on Jul. 2, 2002, for example, which are incorporated by reference herein, in their entireties. The patient has unobstructed side-to-side views and there is room in the gap for patients to extend their arms, which helps them to relax. Claustrophobic reactions are decreased and it is easier for the patient to lie still without sedation. Obese and pregnant patients can be more easily accommodated, as well. The patient is also easily accessible by a technician or a doctor, which assists in positioning the patient. This patient accessibility is also advantageous in case of emergency.

Despite these advances in MRI assembly design, it has been found that patients still experience claustrophobia and have difficulty remaining motionless due to the surroundings. Since any motion of the patient interferes with the image clarity, there still remains a need in the art to calm a patient during the MRI procedure.

SUMMARY OF THE INVENTION

The present invention imparts calmness to a patient during a medical procedure, such as an MRI procedure.

In accordance with one embodiment of the invention, a room is disclosed for use in conducting a medical procedure. A screen is disposed in the room for providing a view of an image, such as a panoramic scenic image, to calm the patent. The image on the screen may be a pictorial scene, a geometric shape, a color or any other image that may calm the patient. The wall is preferably arcuate to enhance the panoramic appearance of the image. The view assists in giving the patient a virtual reality feeling of being part of the scene on the screen, and not in a medical procedure room.

Accessory devices such as lighting, acoustic and scent devices may be included to further the calming effect. The theme of the image, and hence its calming effect, may be further enhanced by having the accessory devices provide lighting, sounds and smells related to the theme. However, the use of accessory devices may still increase the calming effect, even if they are not related to the theme of the image.

The medical procedure may be MRI, in which case at least the imaging volume of an MRI assembly is within the room. The MRI assembly may be an open MRI assembly having first and second poles that may be painted or otherwise decorated to correspond with the theme of the image to further the calming effect on the patient. The poles may also be painted or otherwise decorated in a manner which does not correspond with the theme of the screen, but may still calm the patient.

In another embodiment, the medical room is defined by an open MRI assembly. The assembly comprises opposing ferromagnetic elements connected to opposing ferromagnetic pole supports. A first magnetic pole and a second magnetic pole are supported by respective pole supports. Opposing walls of the room are defined by the opposing ferromagnetic elements of the assembly and the ceiling and floor of the room are defined by the opposing pole supports of the assembly. The poles extend into the room.

BRIEF DESCRIPTION OF THE DRAWINGS

FIG. 1A is a perspective, partial cutaway view of a room for conducting a medical procedure, in this case MRI, in accordance with one embodiment of the invention;

FIG. 3A is a partial top view of the room of FIG. 1;

FIG. 3D is a partial front view of the room of FIG. 3C;

FIG. 9A is an enlarged front and top view of a portion of the cartridge in FIG. 9;

DETAILED DESCRIPTION OF PREFERRED EMBODIMENTS

FIG. 1A is a perspective, partial cutaway view of a room 4 for conducting medical procedures in accordance with one embodiment of the present invention. In a preferred embodiment, the room 4 is defined by an open magnetic resonance imaging ("MRI") assembly 10 and the medical procedure is an MRI scanning procedure. The MRI scanning procedure may be conducted in conjunction with other medical procedures, as well.

Figure 1B:
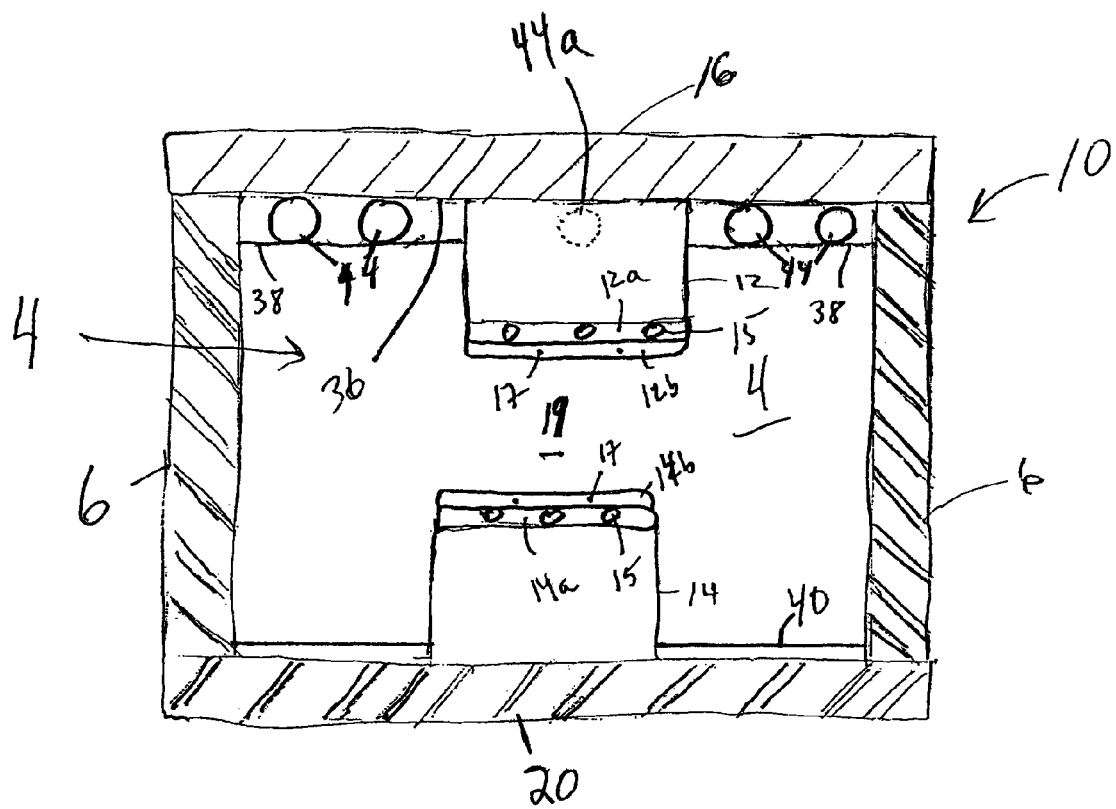
FIG. 1B is a front view of the room of FIG. 1, showing the components of the MRI assembly.

FIG. 1B is a front partial cross-sectional view of the room 4 of FIG. 1A, more clearly showing the magnet assembly 10 defining the room 4. The assembly 10 includes first and second opposed ferromagnetic plates 6. The first and second ferromagnetic plates 6 support a first, upper ferromagnetic pole support 16. The first and second ferromagnetic plates are supported by the lower pole support 20. In FIG. 1A, the top ferromagnetic pole support 16 is not shown to ease illustration of the other components of the room 4. Each pole support 16, 20 supports a respective ferromagnetic pole 12, 14. The plates and pole supports are connected to form magnetic circuits through the poles 12, 14, as is known in the art. Electromagnetic coils (not shown) for generating magnetic fields are typically provided around the pole supports 16, 20, as is known in the art.

In the illustrated example, each ferromagnetic pole supports a plate 12a, 14a of insulative material containing gradient field coils 15. The gradient field plates 12a, 14a may in turn support additional plates 12b, 14b of insulative material, respectively, containing other hardware, such as the windings of a transmitting antenna 17, as is known in the art. Shim coils may also be supported by insulating plates, for example. An imaging volume 19 is defined in the gap between the poles 12, 14 and the associated hardware. A canopy is typically provided over the poles 12,14 and the associated hardware.

The first and second opposed ferromagnetic plates 6 may define two opposing walls of the room 4, while the first and second pole supports 16, 20 may define the ceiling and floor of the room respectively. A dry wall of plaster, for example, (not shown) may also be provided between the ferromagnetic plates 6 and the screen, as well. A secondary ceiling 38 may be provided below the pole support 16 and a floor 40 may be provided over the pole support 20, as discussed further, below. The room has an optional back wall 6', which in this embodiment is arcuate.

Figure 2:
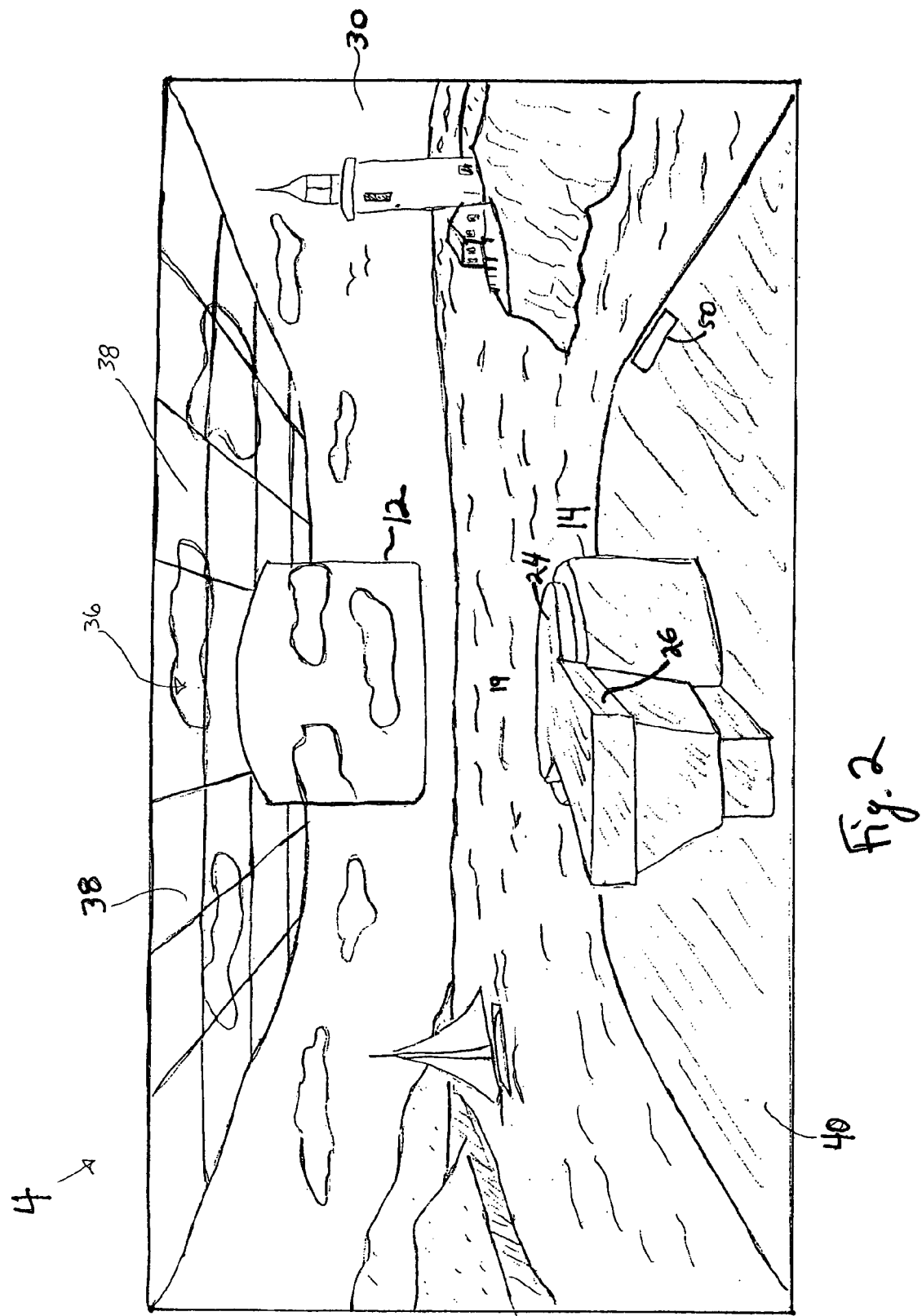
FIG. 2 is a front view of the room of FIG. 1, as it would appear to a patient entering the room.

In accordance with one embodiment of the present invention, a screen 30 including one or more images is disposed in the room 4, as shown in part in FIG. 1A. FIG. 2 is a front view of the room 4, as it would appear to a patient entering the room. FIG. 2 shows the screen 30 and the ferromagnetic poles 12, 14. A patient bed 26 is also shown adjacent to the ferromagnetic pole 14. A portion 24 of the bed 26 rests on top of the pole 14, for supporting at least a portion of the patient in the imaging volume 19.

The screen 30 is supported by a track 70, as shown in FIG. 1A. The track 70 preferably has an arcuate shape that creates a panoramic effect in the image on the screen 30. The screen 30 preferably covers the walls 6 and 6', from the ceiling 36 to the floor 40, as shown in FIG. 2. The view assists in giving the patient a virtual reality feeling that the patient is at the scene in the screen, and not in a medical procedure room. FIG. 3A is a top view of the room 4 of FIG. 1A, better showing the arcuate track 70. The track 70 can be mounted on the ceiling 36 or to the walls 6 and 6'. Holes 71 are preferably provided through the track 70 to reduce the weight of the track.

Figure 3B:
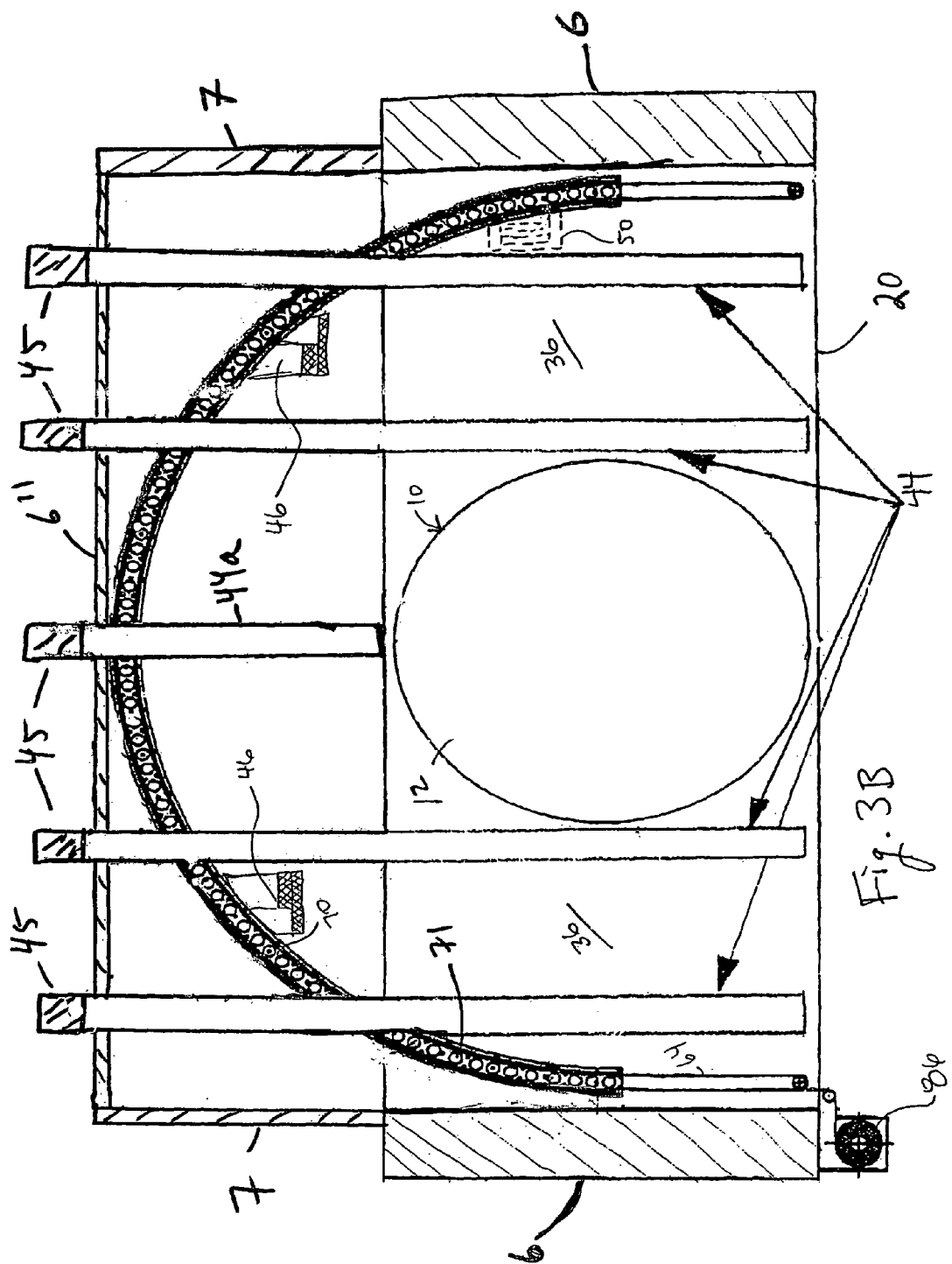
FIG. 3B is a partial top view of a room similar to the room of FIG. 1, except that it has a straight back wall.

FIG. 3B is a top view of a room 4 including a straight back wall 6" instead of the arcuate wall 6'. A straight back wall 6" may facilitate shielding of the room 4. Walls 7 are provided to connect the ferromagnetic plates to the back wall 6".

The screen 30 is stored and delivered from a delivery cartridge 86, shown in the left side of the room 4 in FIG. 1A and in FIGS. 3A and 3B. The delivery cartridge is preferably provided at a side edge of one of the walls 6 of the room 4. Operation of the cartridge 86 and the track 70 to display the screen 30 is described further below. Several images are preferably contained on the screen 30, which are selectively chosen by scrolling the screen across the room 4 to display the desired image. In one embodiment, two to six images are stored on one side of the screen 30. Additional images may be provided on the opposite side of the screen 30. Display of images on the opposite side of the screen 30 is also described, below.

The room 4 is also surrounded with a continuous or substantially continuous electrically conductive shield, commonly referred to as a Faraday shield (not shown). The Faraday shield typically comprises steel panels or a copper mesh, as is known in the art. This shield protects against radio frequency radiation that can interfere with the operation of the MRI assembly 10. The floor 40, the wall 6 and the ceiling 36 may also be provided with conductive elements, such as conductive mesh (not shown).

A window 80a is preferably provided at the front end of the room, as shown in FIG. 1A. A door 82, which may also contain a window 80b, is also provided, to allow entry into the room 4. The door 82 may be situated so that the patient can view the image on the screen 30 as the patient enters the medical procedure room 4. The patient may also see the screen 30 before entering the room. A feeling of calm may thereby be promoted in the patient prior to entry into the room 4. The windows 80a, 80b may also be provided with shielding. A wall 81 containing the door 82 and the window 80 may be slightly separated from the ends of the ferromagnetic plates 6, as shown in FIG. 1A, or may be substantially flush against them.

The door 82 and window 80 may also contain conductive coverings, such as a copper mesh (not shown) in the door and a conductive film on the window. The equipment disposed inside the room 4, and hence inside of the Faraday shield, is also preferably suitably designed for low radio frequency emission to minimize interference with the operation of the MRI assembly 10.

In addition, an odor emitter 50 may be provided on the floor 40 or the ceiling 36 to emit odors which may calm the patient, as in aromatherapy. Odor emitters 50 are shown in FIG. 1A, FIG. 2 and FIG. 3A. The odors may also relate to the theme of the screen 30. In one implementation that uses a seaside image, for example, smells common to the sea, such as salty ocean water, could be emitted from the odor emitter 50.

The odor emitter 50 may be linked with an air vent for distributing the aroma into the medical procedure room, as well. The odor emitter 50 may be disposed behind the shielding, for example, in fresh air vents, and hence would not require a design for low radio frequency emission. If provided on the floor 40, as shown, the odor emitter 50 should be designed for low radio frequency emission. In another alternative, the odor emitter 50 may be disposed between the panels 38 and the top pole support 16. The odor emitter 50 could be protected by the mesh shield.

FIG. 1A also shows a controller 34 located outside the room 4, protected by the shield. The controller 34 controls the MRI assembly 10 and/or the movement of the screen 30. Alternatively, a separate controller can be provided for the screen 30. The screen controller may merely be a switch with a forward and reverse function for moving the screen in those directions. Speed control may be provided as well. The switch may be in the room 4 or outside of the room 4.

As mentioned above, several images are preferably stored on the screen 30. The image on the screen may be a pictorial scene, a geometric shape, a color or other such image to facilitate calmness. One or more images on the screen 30 can be geared towards children. Such images may include scenes with cartoon characters, for example. The patient may select a desired image for viewing during the medical procedure, as described further, below. The screen 30 is then scrolled across the wall until the desired image is reached, as described further below.

A plurality of panels 38, also decorated in accordance with the theme of the scenes on the screen 30, are preferably provided below the top ferromagnetic plate 16, forming a secondary ceiling, also shown in FIGS. 1B and 2. For example, the panels 38 may be colored or decorated to represent the sky.

A lighting system is preferably provided between the panels 38 and the top ferromagnetic plate 16, as shown in FIG. 1B, FIG. 3A and FIG. 3B. The lighting system may comprise one or more light tubes 44 secured to the ceiling or wall. The light tubes 44 may also be fiber optics. In one implementation, a light emitter 45 is connected to each tube 44, to emit light into the tube. The light tube 44 reflects light emitted by the light emitter 45, out of the side walls of the tubes 44, across the ceiling panels 38. This reflections allows the ceiling panels 38 to better emulate the appearance of the sky. Suitable emitters may be obtained from TIR Systems, Vancouver, Canada under the tradename Series 6000 HID Luminaire, for example, for use with TLP 4 and TLP 6 light guides, also available from TIR systems. The light tubes 44 and emitters 45 are not shown in FIG. 1A, so that other components of FIG. 1A may be more readily seen.

FIG. 3A shows one implementation of the light tubes 44 and the light emitters 45, where the back wall 6' of the room 4 is arcuate. FIG. 3B shown another implementation of the light tubes 44 where the back wall 6' is straight. In both cases, the light emitters 45 are disposed behind the shielding of the wall 6 or the wall 6", respectively, to reduce interference with the MRI assembly 10. Alternatively, the ceiling panels 38 or the light emitters 45 may be provided with shielding. Shielded light emitters 45 may be positioned anywhere in the room 4. The central light tube 44a is shorter than the others, for positioning behind the pole 12. In FIGS. 3A and 3B, the top pole support 16 is not shown.

Figure 3C:
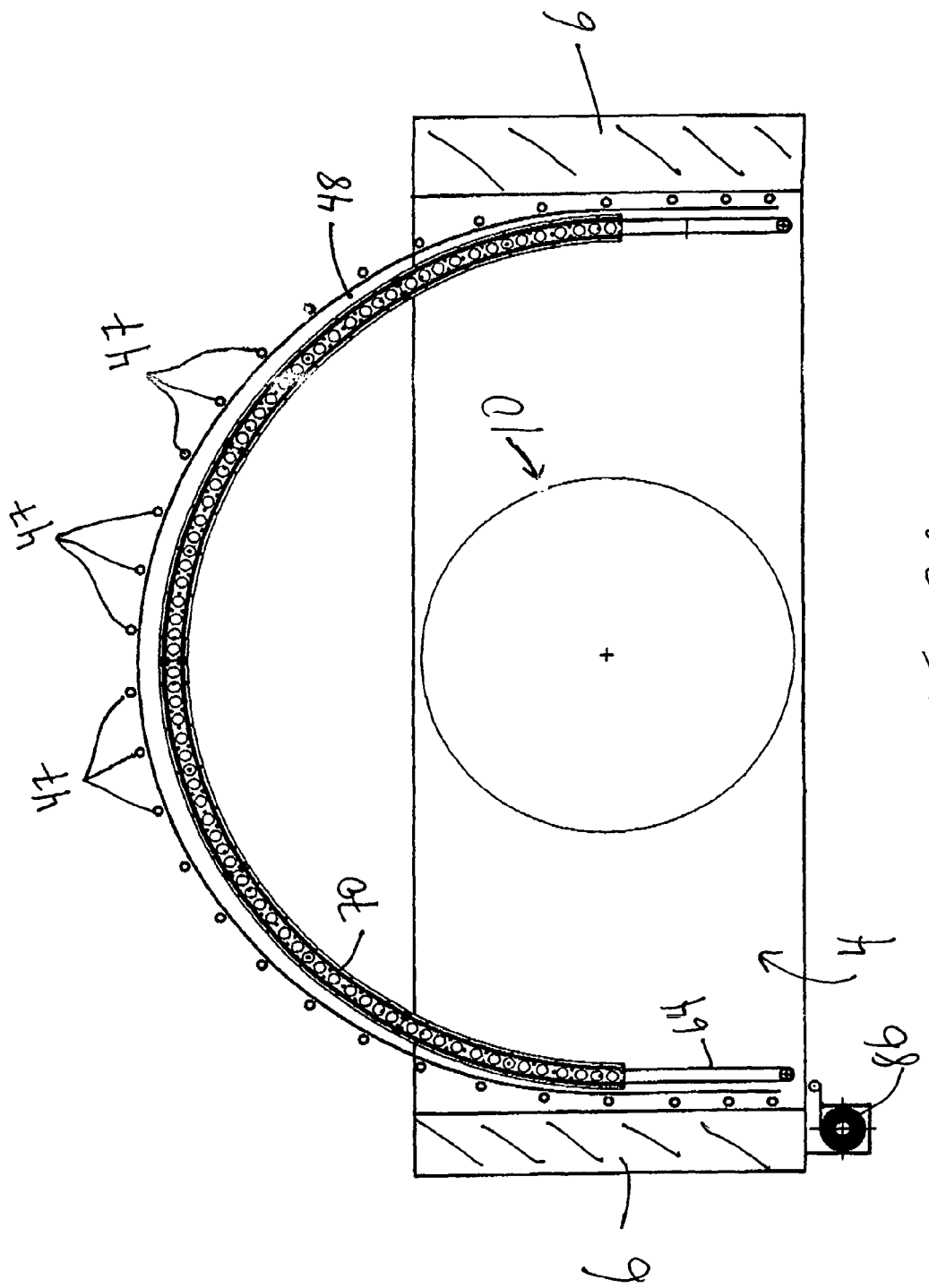
FIG. 3C is a partial top view of a room similar to the room of FIG. 1, showing a lighting system behind the screen.
Figure 3B:
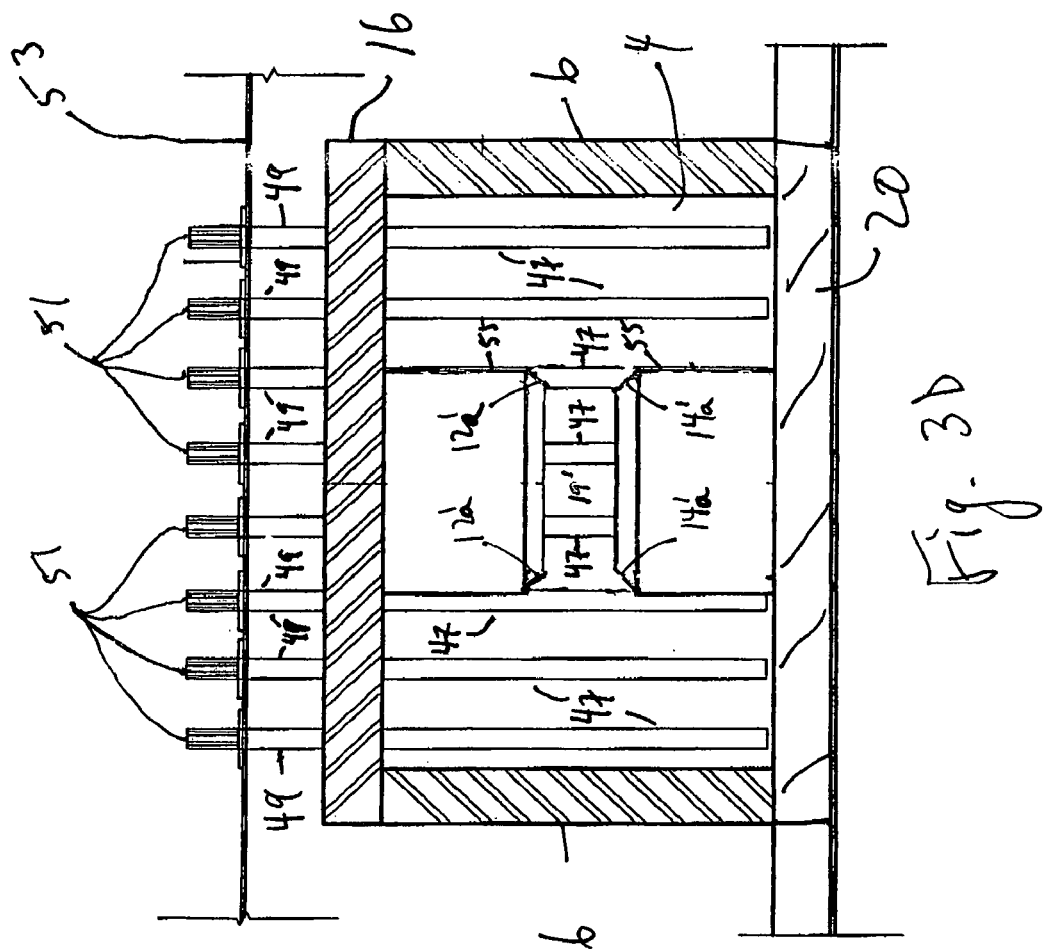

Alternatively or in addition to providing a lighting system above the panels 38, a lighting system may be provided behind the screen 30 to illuminate the screen. FIG. 3C is a partial top view of an MRI room 4 showing light sources 47 behind the screen 30. The light sources 47 may be the light tubes and the light emitters described above or a fluorescent lighting system, for example. A layer 48 of a fabric for diffusing the light emitted by the light sources is preferably provided, particularly when fluorescent lights are used. Fluorescent lights can only be used when an MRI procedure is not being conducted because of interference with the MRI system. However, a fluorescent lighting system that is on while the patient enters the room, approaches the imaging volume 19 and is being positioned for the procedure, could contribute to the calming effect of the invention. The back wall of the room 4 may be arcuate, as in FIG. 3A, or straight as in FIG. 3B. In FIG. 3C, the top pole support 16 is not shown.

FIG. 3D is a partial front view of the room 4 of FIG. 3C with the screen 30, diffusion fabric 48 (if provided) and delivery cartridge 86 removed, wherein the light sources 47 are light tubes 49. Light emitters 51 are shown connected to the light tubes 49. The light emitters 51 are preferably located above a shielding material 53 to substantially reduce or eliminate interference with the operation of the MRI assembly 10. As mentioned above, a canopy is typically provided over the poles and the associated hardware. In FIG. 3D, a canopy 55 is provided over the poles 12', 14' and associated hardware (not shown). The canopy 55 has an optional tapered circumferential edge 12a', 14a' that provides additional room for personnel to access the patient in the imaging volume 19'. Each tapered edge 12a', 14a' may have a width of 3-6 inches, for example. The tapered edges 12a', 14a' need not extend completely around the circumference of the canopy. It may be provided only at portions of the canopy where personnel are likely to access the patient.

An acoustic means, such as speakers 46, may be disposed on the ceiling 36 against the wall 6. (See FIGS. 1A, 3A and 3B.) Again, the speakers 46 can be disposed anywhere inside or outside the room, depending on whether the speakers contain shielding or are designed to emit low RF signals to minimize interference. The speakers 46 emit sounds that may further calm the patient. The sounds may relate to the theme of screen 30. For example, if the screen 30 depicts a seashore scene, the speakers 46 can supply sounds of the seashore; such as the sounds of waves hitting the shore, boat noises, and seagull sounds. The sounds may also be music, which may also be selected by the patient. The speakers 46 may or may not contain shielding. However, like the light emitters 44, if no shielding is provided, the speakers 46 should be suitably designed for low radio frequency (RF) emission to minimize interference with the operation of the MRI assembly. The tapered edges 12a', 14a' may not extend completely around the canopy 55. It may be provided only around the portions of the canopy where it is likely that personnel will access the patient.

Figure 4:
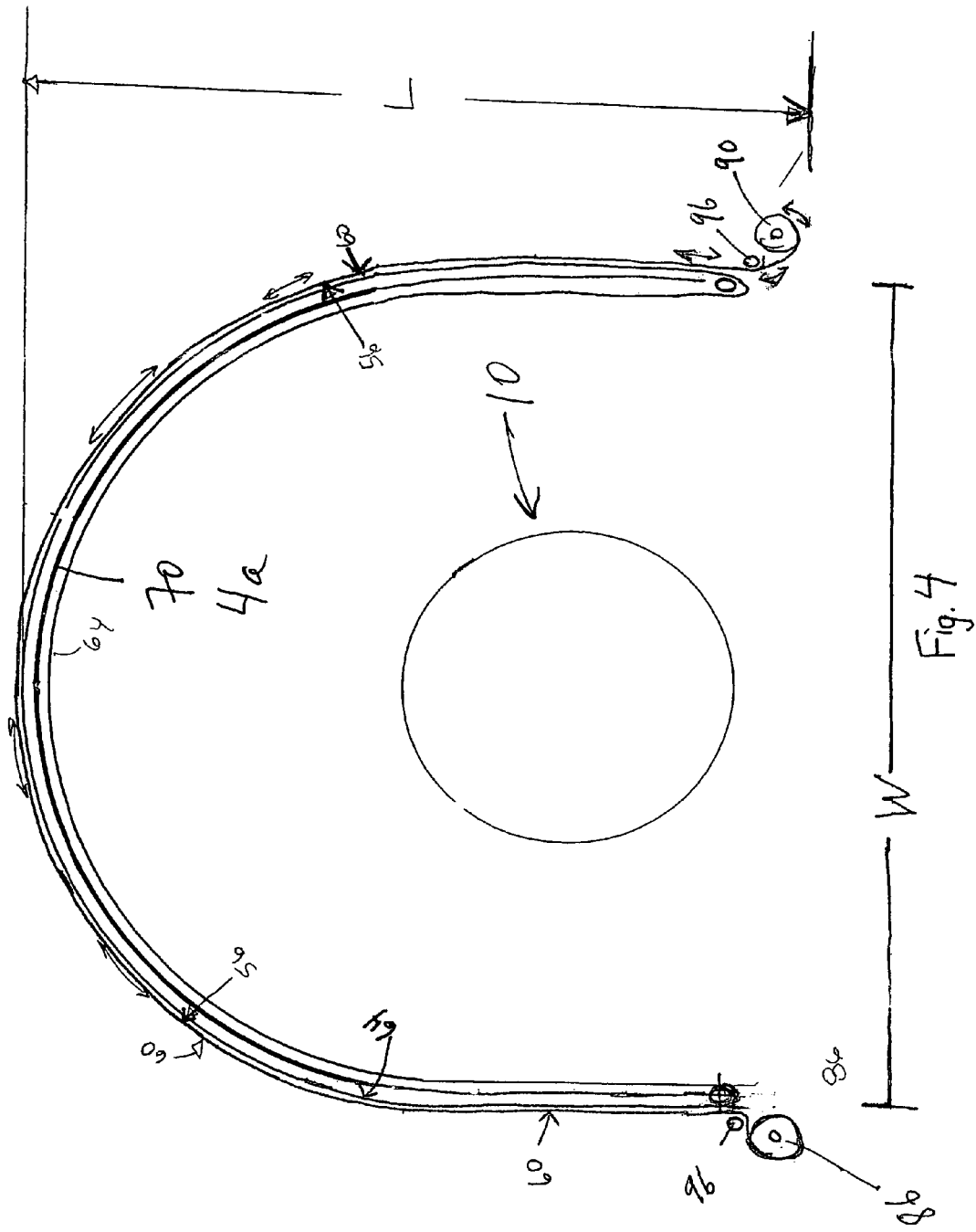
FIG. 4 is a modified view of a portion of either FIG. 3A or FIG. 3B, illustrating a one-sided screen.

As shown in FIGS. 1A, 1B and 4, room 4 has a height "H", a length "L", and a width "W". In one configuration, the height "H" of the room is about 8 feet, the length "L" is about 12 feet and the width "W" is about 14 feet.

The bed 26, discussed above with respect to FIG. 2, may be a typical bed used in MRI. Preferably, the bed can move into and out of the imaging volume 19, can rotate in either direction about a polar axis through the poles 12, 14 of the MRI assembly 10, can move along a plane perpendicular to the polar axis and can tilt about a longitudinal axis of the bed. Thus, a patient can be disposed in any radial direction with any part of the patient's body in the gap 19 between the pole surface 22 and the pole surface 24. A suitable bed is described in U.S. Pat. No. 6,208,145, for example, assigned to the assignee of the present invention and incorporated by reference, herein. The bed can be decorated to further the theme of the image or scene on the screen, as well.

The MRI assembly 10 can also be decorated to promote a feeling of calm. The decoration may or may not relate to the theme of the image. For example, in the implementation shown in FIG. 2, the first pole 12 is decorated to resemble sky and clouds. The second pole 14 is decorated to resemble a wooden boardwalk on a shore. The decoration may be provided on the canopy over the poles and associated hardware.

The floor 40 can be similarly decorated as the pole 14 and the bed 26. The floor 40 can be decorated by paint or other methods known to those skilled in the art of floor decoration. Depending on the implementation, the floor 40 can be comprised of replaceable floor panels that may also be decorated to emulate the theme of the screen. In one embodiment, the floor panels can be easily changed to coordinate with the image chosen. In another variant, the floor is decorated a neutral color or pattern to match any screen image, avoiding the need to change the decoration on the floor.

As discussed above, panels 38 are provided below the top ferromagnetic plate 16. In FIG. 2, the ceiling is decorated to coordinate with the theme of the images on the screen in the cartridge. The ceiling panels may be replaced to change the decoration on the ceiling to coordinate with a different set of images displayed on another screen cartridge. The light from the light tubes 44 is transmitted through the ceiling panels 38 to further the theme of the screen. The light can be made to pulse intermittently to mimic the change in sunlight due to the shading effect of clouds. SUMMER SKY ENVELITE® translucent panels, said to be acrylic, which is 0.80 inches thick, available from Envel Design Corporation, Westlake Village, Calif., catalog number 6991-HE, may be used, for example.

Figure 9:
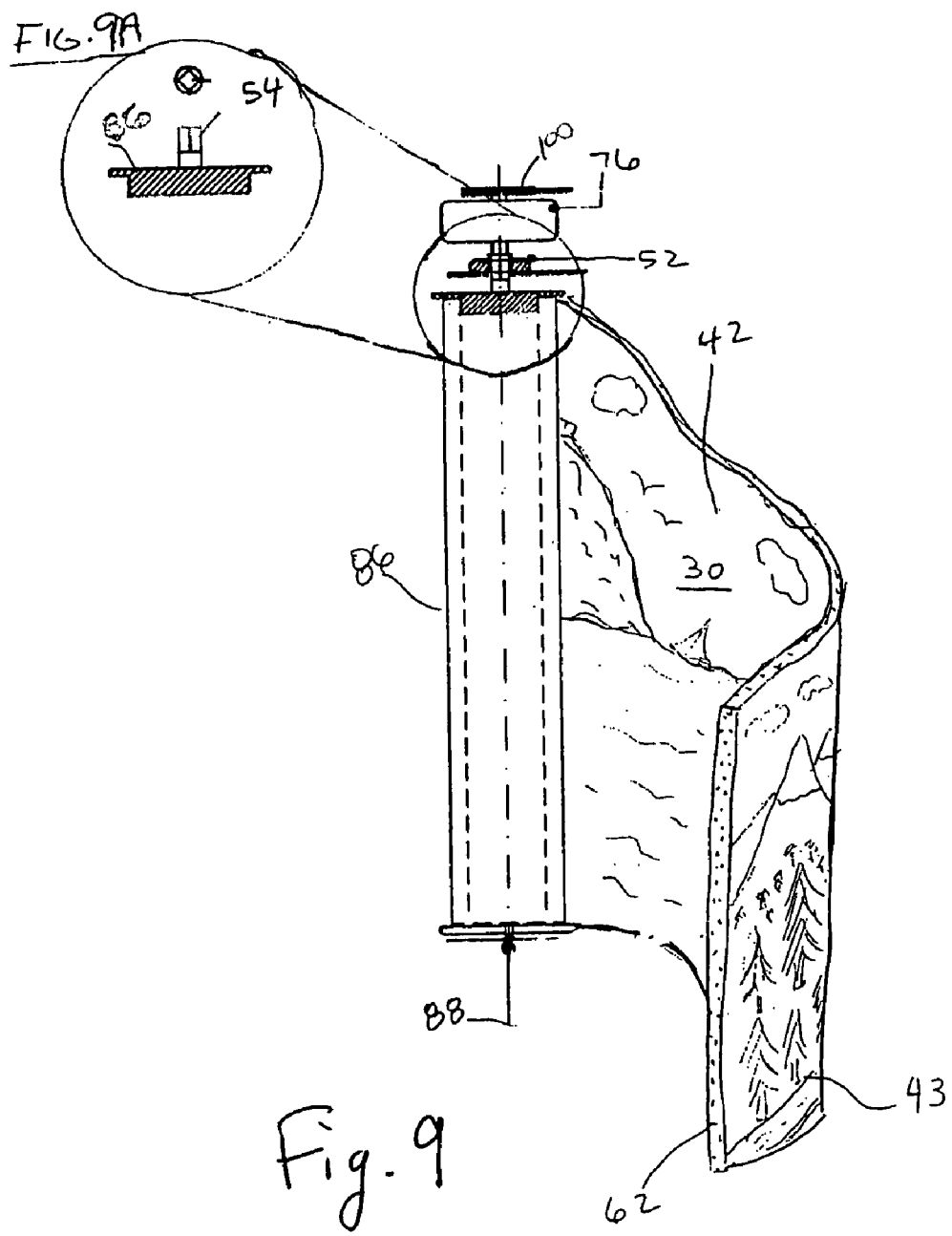
FIG. 9 is a front perspective view of a delivery or take-up cartridge in accordance with one embodiment of the invention.

The screen 30 may contain about 2 to 6 different images on each side of the screen and measure to about 32 feet long, for example. Images can be printed on one side of the screen or both sides of the screen, as shown in FIG. 9. The screen 30 in FIG. 9 illustrates a first pictorial scene or image 42 and a second pictorial scene or image 43. The images can be different, as shown in FIG. 9, or the same, depending on the implementation. The screen 30 may further contain or be coated with anti-microbial agents 62, which resist bacteria and allow the medical procedure room to maintain its sterility. The screen can be made of various materials, including, polyester, woven polyethylene, textile fabric, natural and manmade fibers. Preferably, the screen is flame resistant and made of an optic white polyester. In this implementation, images can be printed on the polyester screen. Poly Screen, said to be a 100% polyester, flame resistant fabric material available from Dazian, New York, N.Y., may be used, for example. The image or images may be printed directly on the material.

Light tubes 44 may also be provided behind the screen to illuminate portions of the screen and accent the theme of the screen. For example, the appearance of the reflection of the sun off a body of water can be reproduced, or light from a sunset or sunrise can be emulated. In these embodiments, the screen material allows light to be transmitted through the image.

In another implementation, the screen 30 can be a laminated sheet, a laminated film, a thermoplastic sheet, a thermoplastic film, a decorated sheet, a decorated film, a wallpaper, a mural, a stained glass, a holographic image, a video projection, a laminated wall, or a decorated wall.

Video imaging or projection, electronic projection, laser lights, and holographic imaging can enhance the image on the screen or be used in place of the screen. In one variant, video projection can be used to superimpose moving images on the image on the screen.

FIG. 4 is a top view of an implementation where the screen 30 has images on only one side. The screen 30 has a first side 56 facing the interior 4a of the room 4 and a second side 60, facing away from the interior 4a of the room 4. The first side 56 has an image or multiple images and the second side is intentionally left blank. In one variant, the screen is transported around the track in a clockwise direction by a moving belt 64. Transport of the belt 64 and hence the screen 30 in a counter clockwise direction may also be provided. The screen 30 is advanced along the track 70 until the desired image faces the interior 4a of the room 4. The screen 30 is dispensed from the delivery cartridge 86 around a guide roller 96, through the track 70, around another guide roller 96 to a return or take-up cartridge 90. The screen 30 is rolled up in the cartridges 86, 90, about a central rod (not shown), as film is rolled in a film cartridge. The central rod may be a plastic or cardboard material. Both the delivery and take-up cartridges are removable for allowing various screens to be used on the belt/track system. Thus, in this implementation, the screen is allowed to scroll across the wall showing one side of the screen 30. Forward and reverse motion is available to advance and retract the screen 30 so that a desired image faces the interior 4 of the room. However, in this embodiment, the screen 30 moves in only one direction, from the delivery cartridge 86 to the take up cartridge 90. A pulley system 72a, 72b provides continuous transport of the belt around the track 70 and assists in transporting the screen 30 from the delivery cartridge 86 to the take-up cartridge 90, as described further below.

Figure 5:
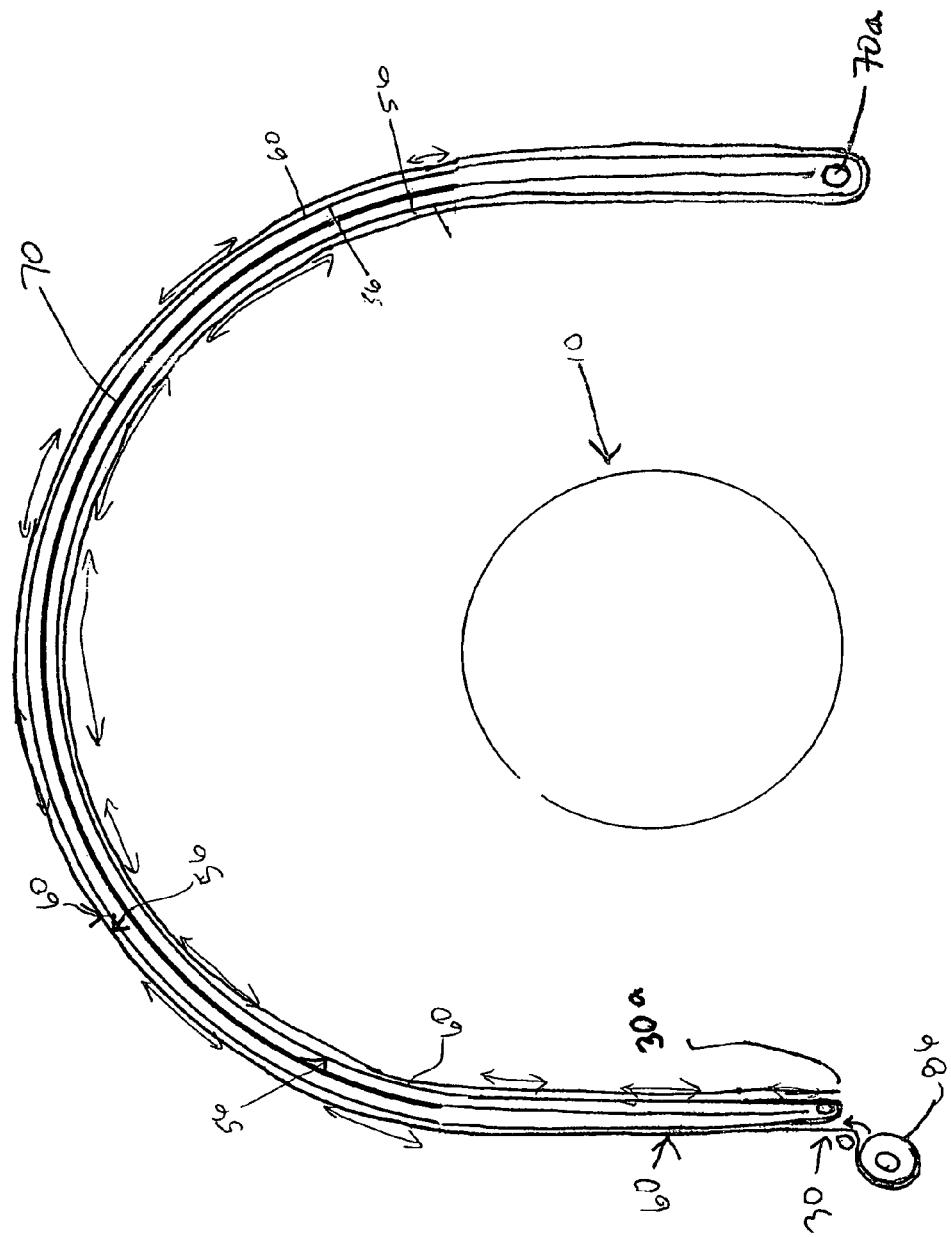
FIG. 5 is a modified view of a portion of either FIG. 3A or FIG. 3B, illustrating a two-sided screen.

FIG. 5 is a top view of an implementation wherein the screen 30 has images on both sides. The screen 30 may be scrolled forward around the track 70 in a first direction, and then back around the track 70 in a second direction opposite the first direction. This double-sided screen 30 provides more images for the patient to choose from. Unlike the system in FIG. 4, this implementation has no take-up cartridge 90.

The arrows in FIG. 5 show the directions of the movement of the screen 30 across the room 4. When the screen is initially dispensed from the delivery cartridge 86, the screen is drawn around the rear side of the track 70, exposing the first side 56 to the patient for viewing. When the screen 30 reaches the end of the track 70, the screen is carried around the end 70a of the track 70 and along the front side of the track 70, exposing the second side 60 to the patient for viewing. As the portion of the screen 30 displaying the second side 60 makes its way across the room 4, it will block the first side 56 from view. A limit sensor or an optical sensor (not shown) may be provided at or near the beginning of the left side of the track 70, to detect when the leading edge 30a of the screen reaches that point, as shown in FIG. 5. Withdrawal of the screen 30 from the cartridge 86 may then be stopped automatically by the controller 34. The next time the system is activated, the direction of travel of the screen 30 may be automatically reversed.

Figure 6:
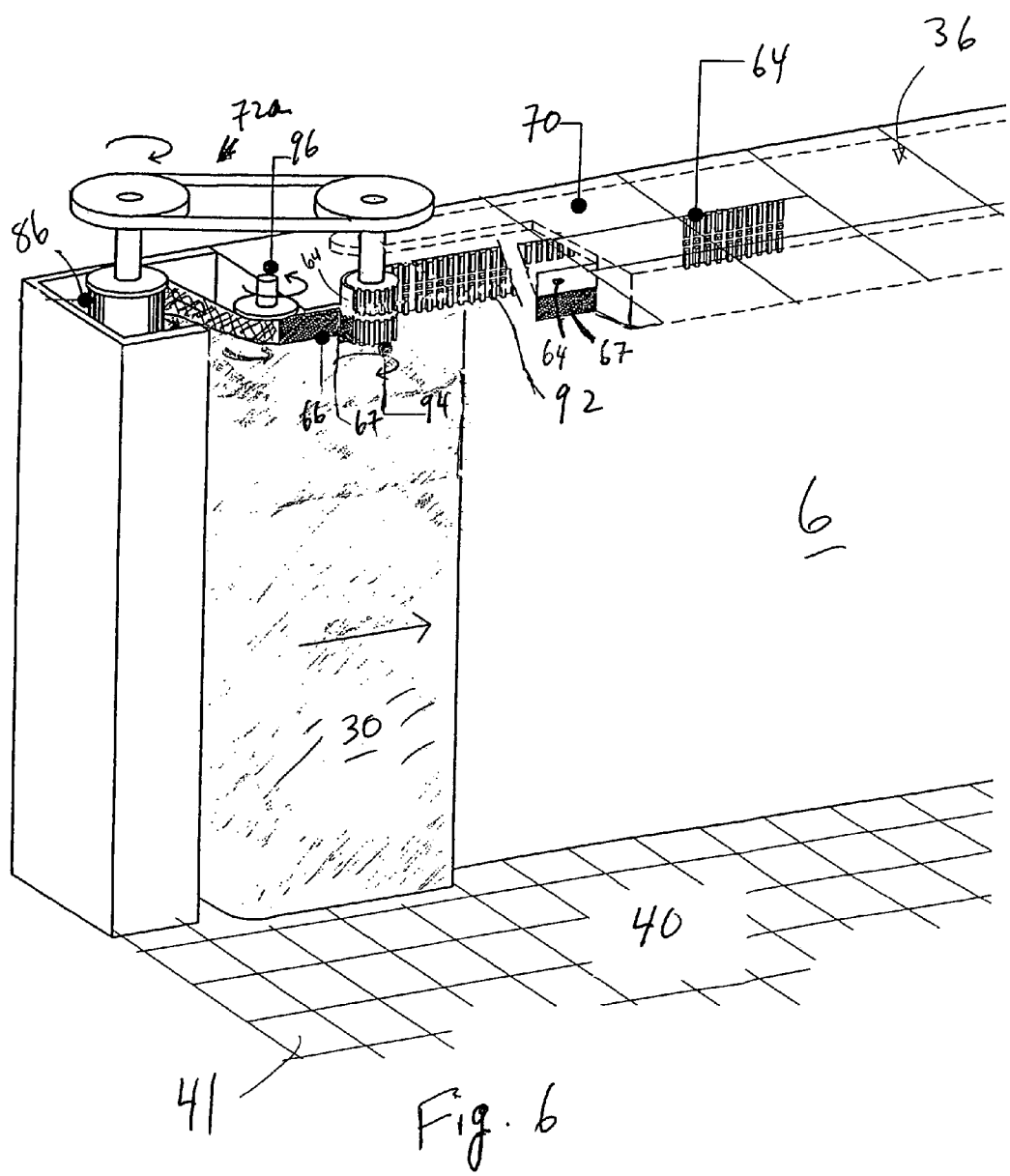
FIG. 6 is a partial perspective view of one side of the room in accordance with one embodiment of the invention, showing how the screen is delivered from a delivery cartridge to a belt for movement along a track.
Figure 7:
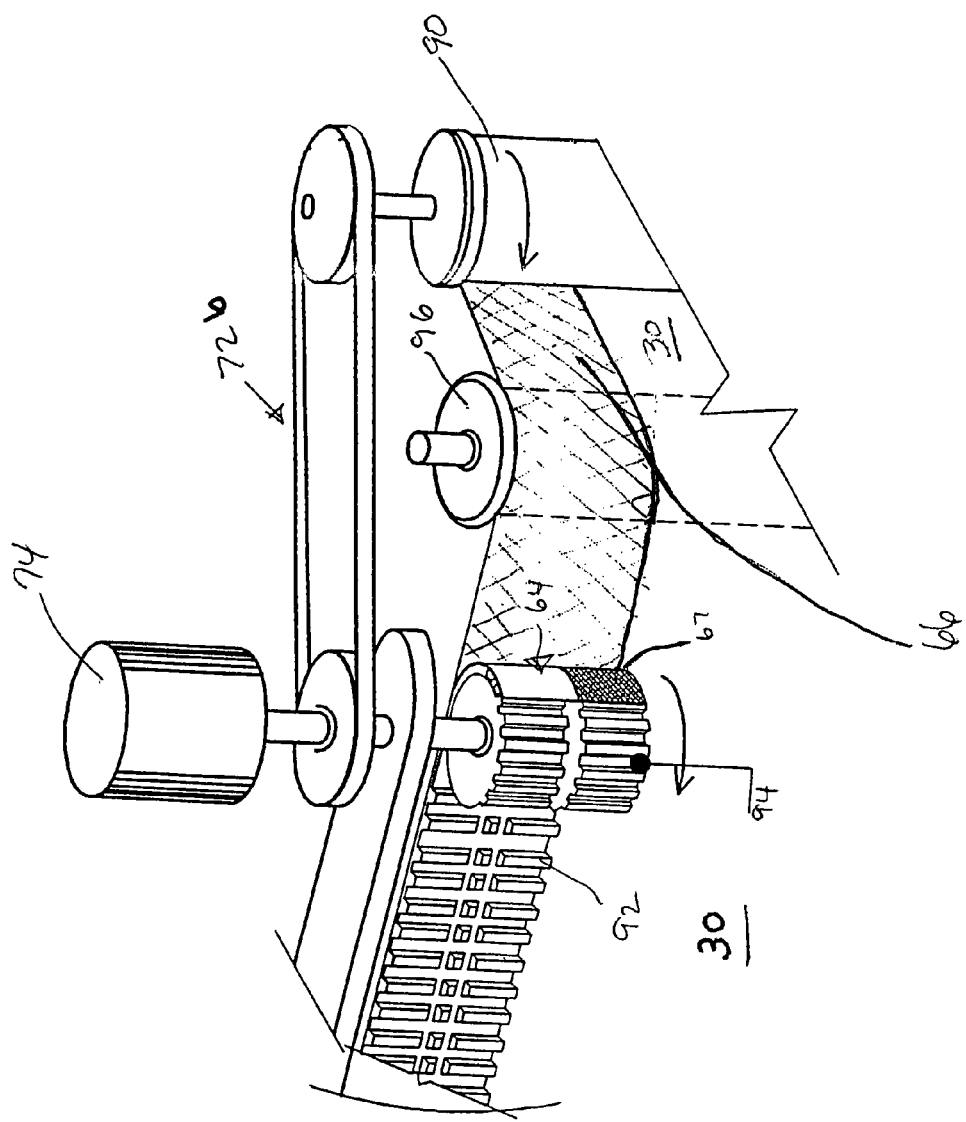
FIG. 7 is an enlarged partial perspective view of one side of the room in accordance with one embodiment of the invention, showing how the screen is removed from the belt and stored within a take-up cartridge.

FIG. 6 is a more detailed view of the delivery cartridge 86, showing how the screen 30 is delivered from the cartridge 86 and attached to the belt 64 in accordance with one embodiment of the invention. FIG. 7 is a more detailed view of the take-up cartridge 90 and associated pulley system 72b, showing how the screen is removed from the track and stored in the take-up cartridge 90.

Preferably, the screen 30 contains an attachment means to removably attach the screen to the belt 64. In this implementation, a hook and loop strip 66 is bonded to the top of the screen. The hook and loop strip 66 mates with another hook and loop strip 67 on the belt 64. The hook and loop strip is VELCRO®. The pulley system 72a causes rotation of the delivery cartridge 86 and the dispensing screen 30. The screen 30 is guided to the belt 64 by a guide roller 96. As the leading edge of the screen 30 moves towards the belt, the VELCRO® strip 66 on the screen 30 is manually attached to the VELCRO® strip 67 on the belt 64. Once attached, the belt 64 pulls the screen from the cartridge 86, across the room 4. VELCRO® allows easy attachment and removal of the screen 30 from the belt/track system. The engagement of the VELCRO® strips 66, 67 with each other is accomplished by compression of the screen onto the belt as the screen is advanced from the delivery cartridge 86. VELCRO® strips are available from McMaster-Carr Supply Company, New Brunswick, N.J., for example.

Various delivery cartridges 86 containing screens with different images can be used.

Other means for attaching the screen to the belt/track system includes hooks, loops, buttons, latches, fasteners, zippers, an adhesive, a snap fit, a knot, a hinge, a bolt, a cable, a clamp, a dowel, a pin, a seam, a rivet, a screw or a nail. However, not all means are detachable, or available for use with an automatic advancing system such as described above.

The pulley systems 72a, 72b drive serrated gears 94 that mate with serrated portions 92 of the belt 64. As the pulley system 72 rotates, the serrated gears 94 rotate, moving the belt 64 in a continuous motion around the track 70.

The track 70 is mounted to the ceiling 36 or to a wall 6, 6', or both. The track 70 could also be mounted to the floor 40.

FIG. 7 shows a take-up cartridge 90 winding up the screen 30 after the strip 66 is detached from the strip 67. Preferably, the screen 30 is removed from the belt 64 at a location adjacent to the point where the belt 64 turns around the track 70 to return to the front side of the track. A guide roller 96 guides the screen towards the take-up cartridge 90 for removal of the screen 30 from the strip 67. The guide roller also allows tension to be applied to the screen 30. This tension allows the screen to be pulled off the belt and the VELCRO® strip 67 as the screen 30 is wound around the take-up cartridge 90. The screen 30 may be attached to the central rod of the take-up cartridge 90 in any one of a variety of manners apparent to one of ordinary skill in the art. In a preferred technique, both the leading edge of the screen 30 and the central rod include matching strips of VELCRO®.

During set up, a cartridge 86 is selected and mounted. The screen 30 is manually advanced from the cartridge 86 around the guide 96. The VELCRO® strip 66 on the screen 30 is attached to the VELCRO® strip 67 on the rear side of the belt 64. The length of the screen 30 is preferably adjusted to accommodate an initial portion of the screen that needs to be wound around the take-up cartridge during setup. That initial portion of the screen preferably does not include an image. Advancement of the belt, here in a clockwise direction by the pulley system 72a, draws the screen 30 from the cartridge 86 around the track 70. When the leading edge of the screen 30 reaches the end 70a of the track 70, the edge of the screen is removed from the belt 64 and manually led around the guide 96, to the take-up cartridge 90. The leading edge of the screen 30 is attached to the central rod of the cartridge 90. Continued advance of the screen 30 from the delivery cartridge 86 to the take-up cartridge 90 causes additional portions of the screen to be rolled around the cartridge, displaying the image or images. The previously displayed portions of the screen 30 are rolled up in the take-up cartridge 90.

The belt 64 may be moved in a forward and reverse direction (clockwise and counter-clockwise, respectively, for example), by a reversible motor 74, as is also shown in FIG. 7. Depending on the implementation, the motor may be either positioned on the right or left side of the room, to drive either the pulley system 72a connected to the delivery cartridge 86 or to the pulley system 72b connected to the take-up cartridge 90. In this example, the motor 70 is positioned on the right side of the room adjacent to the take-up cartridge 90. Preferably, the motor is positioned out of the view of the patient, for example, above the ceiling. The motor turns the pulley system 72, which turns the serrated gear 94 and the take-up cartridge 90.

The motor 74 is preferably a direct current (DC) motor. A DC motor is energized by direct, constant currents and voltages. An alternating current (AC) motor, in contrast, is energized by alternating, time-varying currents whose time average values are zero. Time-varying currents and voltages generate electromagnetic fields that can interfere with the operation of the MRI system. Traditional DC motors have been built using field windings and an armature which is energized by brushes. Maintenance is not a concern unless the traditional motors are run in a harsh environment. Most DC motors are designed for specific applications where a specific horsepower and speed is required.

A DC motor need not include brushes. In a brushless DC motor, a series of permanent magnets with alternating polarities are arranged in a ring. The magnets set up a static flux field on a rotor within the ring. Electromagnetic coils are wound around the rotor. As the polarity of the electromagnetic coils is switched, the rotor will be repelled by certain of the magnets and attracted by others. The arrangement of the magnets and the timing of the switching causes rotation of the rotor. A DC motor used in the present application for the belt/track system provides the advantages of minimal electromagnetic interference from arcing with the magnet, and quiet operation. These advantages of the DC motor minimize interference with the MRI assembly and the medical procedure. A one-half horsepower motor has been found to be appropriate. The motor may be Model No. 5640352543 motor, available from DNB Motor and Control Corporation, New York, N.Y., which has a maximum RPM of 1725, for example.

Figure 8:
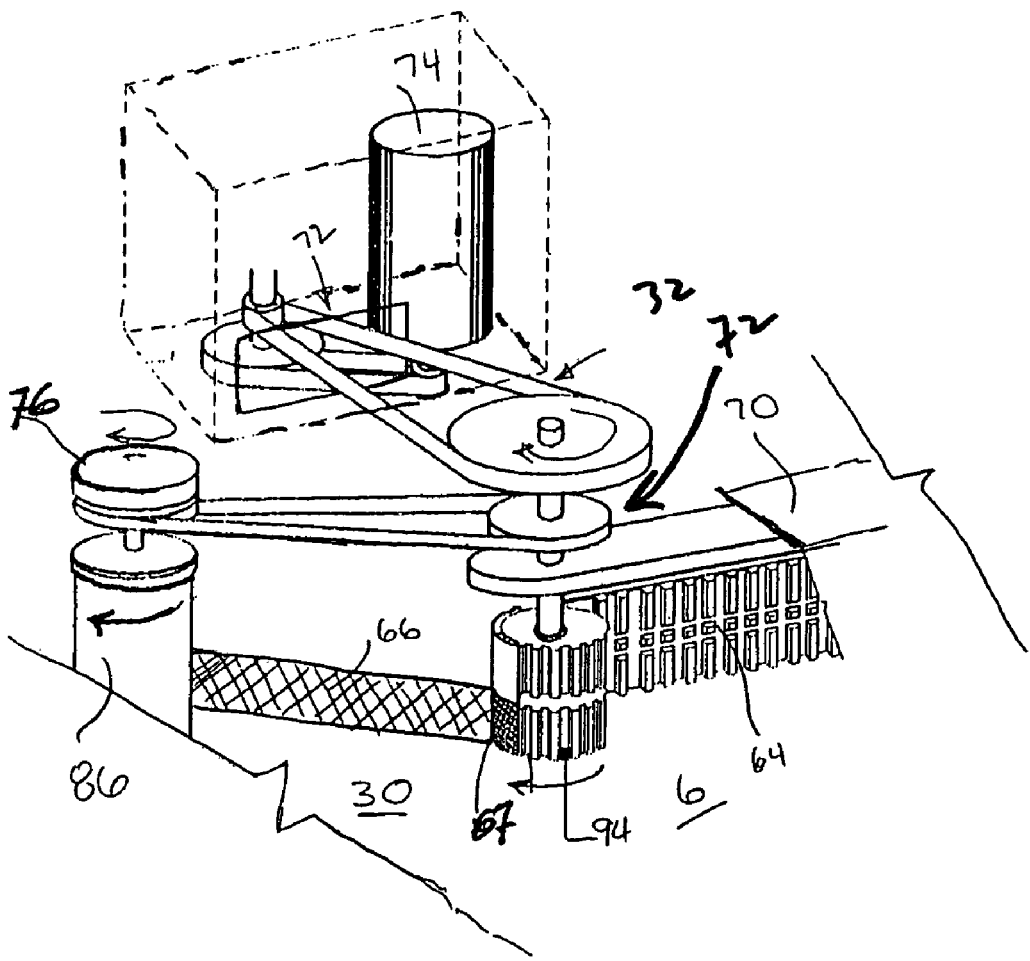
FIG. 8 is an enlarged partial perspective view of the take-up cartridge and associated components in accordance with another embodiment of the invention.

FIG. 8 illustrates an embodiment where the motor 74 is positioned on the left side of the wall 6, to drive the pulley system 72a connected to the delivery cartridge 86. The motor 74, the pulley system 72a and a gear reduction unit 32 coupling the motor 74 to the pulley system 72 are shown. A torque converter 76 is also preferably coupled to the pulley system 72a. The torque converter 76 controls the speed of the screen 30 and stops movement of the screen 30. The torque converter 76 is optional since the gear reduction unit 32 can adequately control the speed of the screen 30 and stop the screen, as well. In this arrangement, the delivery cartridge 86 is aligned with the belt 64 and the track 70 so that a guide roller 96 is not needed. It is readily apparent that the position of the delivery cartridge 86 with respect to the belt 64 and the track 70 may be changed in this embodiment to require a guide roller 96, as in the configuration of FIG. 6, for example.

The gear reduction unit 32 provides the horsepower required to move the screen 30. With a one-half horsepower motor, a gear reduction unit providing a gear reduction of about 10:1 to about 20:1 is preferred, with a preferred gear reduction of about 16:1 most preferred. This ratio of gear reduction provides the appropriate speed and power, required to remove the screen from the delivery cartridge 86 and to move the screen across the periphery of the room 4 without sudden jolts that could tear the screen. In the present embodiments, a power of about 181 inch pounds is provided. The screen can be moved at about 1.5 feet per second, for example. The gear reduction unit also enables the screen to be moved to the desired image and to be stopped for viewing by the patient during the medical procedure.

Attachment of the screen 30 to the belt/track system is also illustrated in FIG. 8. The VELCRO® strip 66 on the top of the screen 30 is shown attached to the VELCRO® trip 67 of the belt 64. Compression of the VELCRO® strips 66, 67 between the guide block 104 and the serrated gear portion 94 is sufficient to attach the two VELCRO® strips together as the screen is advanced. Only light compression is required.

FIG. 9 illustrates the delivery cartridge 86 in more detail. Both sides of the screen 30 include images. The screen 30 can have a first pictorial scene 42 and a second pictorial scene 43 containing either the same or different themes. Illustrated for example only are two different images. By printing images on both sides of the screen, a delivery cartridge 86 can deliver a wider variety of images for the patient to choose from. In addition, printing on both sides of the screen reduces the number of delivery cartridges that need to be stored. The screen can also contain anti-microbial agents 62 and other related agents to assist in maintaining the sterility of the medical procedure room. Such other agents could include, for example, flame-retardants, heat stabilizers, anti-oxidants and other related agents.

The delivery cartridge 86 and the take-up cartridge 90 each preferably further include a pillow block 52 and a bearing 88 disposed on opposite ends of the cartridges. These components are used to assist in easily adding and removing the cartridges. A pillow block is a well-known item in the art of mechanical design. A two-bolt flanged pillow block, Serial No. 60005K12, available from McMaster-Carr Supply Company, New Brunswick, N.J., which has a ⅝ inch shaft diameter, may be used, for example.

The pillow block is connected to the torque converter 76. The torque converter and the cartridge are held in place by a holder 100. The bearing 88 below the cartridge 86 may be spring loaded to assist in changing cartridges. The delivery cartridge 86 may further include a square drive 54 disposed on the top of the cartridge, for being received in an entrance of the torque converter. As shown in FIGS. 9 and 9A, the square drive 54 fits into the pillow block 52, aligning the cartridge 86 with respect to the belt/track system. The cartridges can thereby be easily inserted into the system without the assistance of any additional fasteners. The entrance of the torque converter 76 is preferably sufficiently longer than the square drive 54 to enable the cartridges 86, 90 to clear the bearing 88 during attachment and removal of the cartridges 86, 90.

Figure 10:
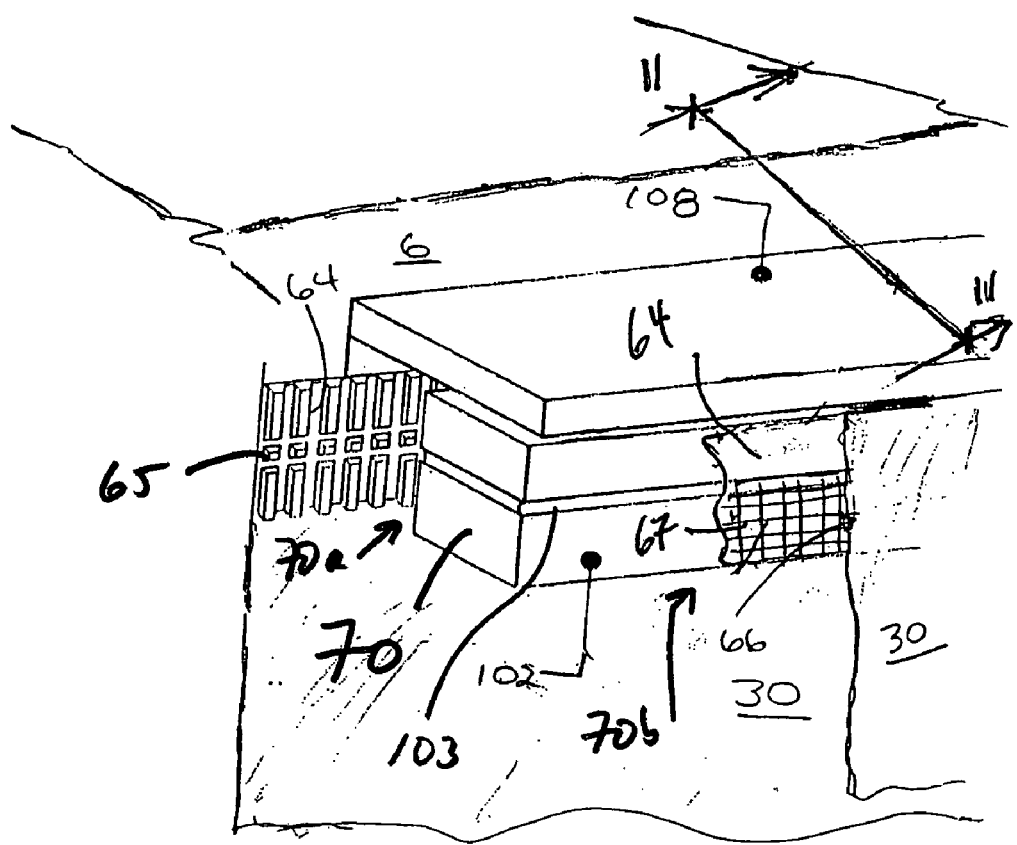
FIG. 10 is an enlarged partial perspective view of one side of the room in accordance with one embodiment of the invention.
Figure 11:
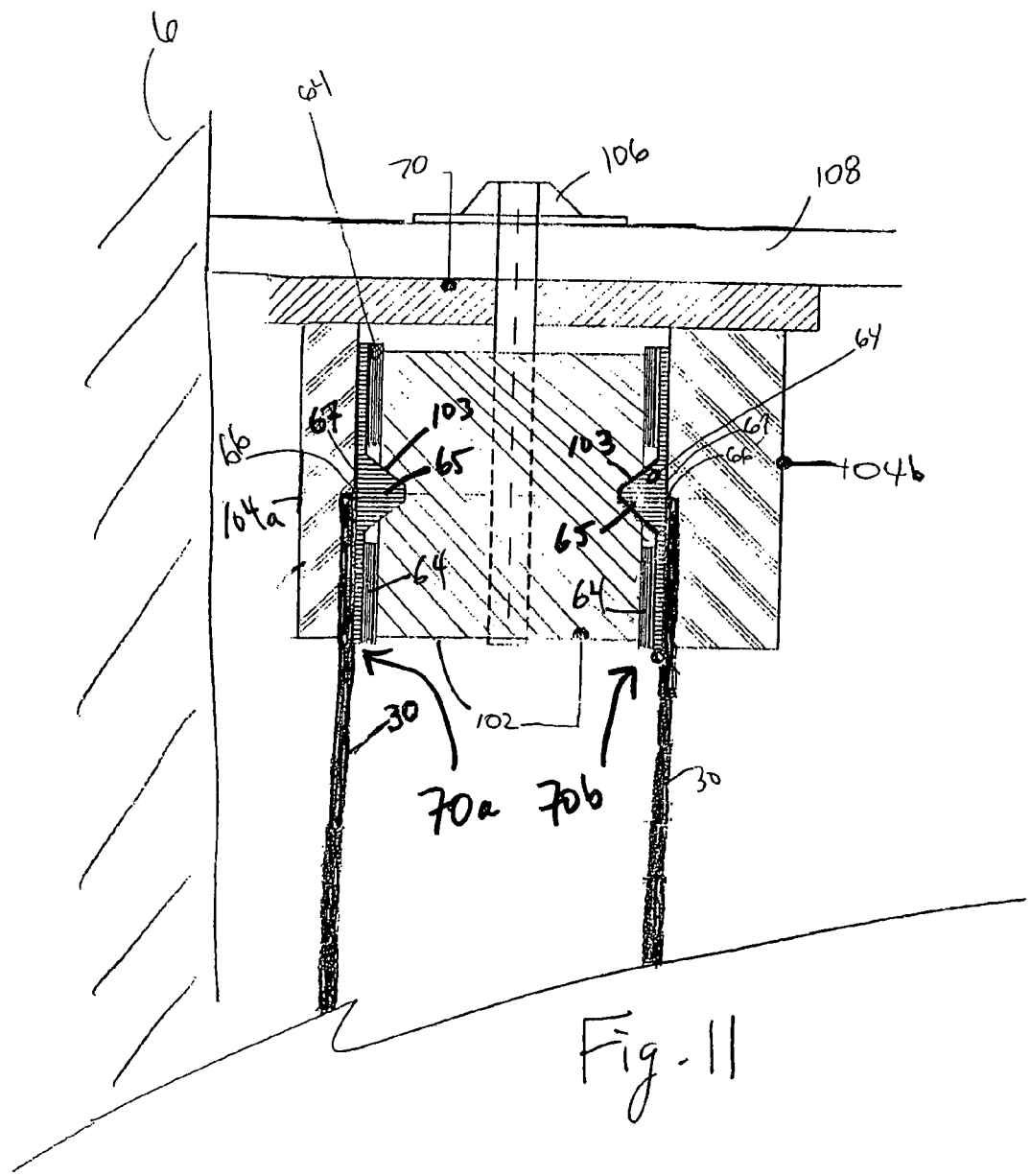
FIG. 11 is an enlarged cross sectional view of FIG. 10 taken along lines 11-11 in FIG. 10.

FIG. 10 is an enlarged view of the belt 64 and an attached screen 30 in relation to the track 70. FIG. 11 is a cross sectional view taken along line 11-11 in FIG. 10. For illustration only, a two-sided screen 30, which travels back to the delivery cartridge 86, is shown. Depicted in both FIG. 10 and FIG. 11 is a track mount 108 that attaches the track to the wall 6, ceiling or both the wall and the ceiling. The track mount 108 comprises an inner guide block 102 between two outer guide blocks 104a, 104b. The outer guide blocks 104a, 104b are spaced from opposing sides of the inner guide block 102 to define two paths for the screen 30 through the track 70. One path 70a is at the rear side of the track 70 and the other path 70b is at the front side of the track 70. The inner guide block 102 preferably includes a groove 103 for receiving a central protrusion 65 of the belt 64, to stabilize the belt 64 as it is moved around the track 70. The guide blocks 104 are attached to the track 70. Fasteners, adhesives, ultrasonic welding and the like may be used to attach these components together.

The track mount 108 is attached to the wall and/or ceiling by any means suitable for such positioning (not shown), such as screws or L-shaped brackets.

The block 102 and the outer guide blocks 104a, 104b are suitably made of a self-lubricating material. For example, such a material may include polypropylene, Delrin, nylon, polyethylene, Teflon, or any combination thereof.

FIG. 11 shows a fastener 106 attaching the mount 108 to the guide track 102. The fastener can be a screw, a bolt, a nail, a dowel, or any other such attachment fastener. The track 70 is disposed beneath the mount 108 in this implementation. The VELCRO® strip 67 on the belt 64 is attached to the VELCRO® strip 66 of the screen 30. However, as previously explained, different attachment means can be utilized to removably attach the screen to the belt.

As discussed above with respect to FIGS. 3A and 3B, holes 71 are preferably provided through the track 70 to decrease the weight of the track. The holes 71 may be provided through the inner guide block 102. The holes 71 are blocked from view in FIG. 10 by the mount 108.

Operation of the room 4 in preparation for use in conducting medical procedures will now be described. An image is selected from a plurality of images on a screen 30 stored in one or more cartridges 86. Preferably, the patient selects the screen from a catalog of images, for example. A technician, doctor or the patient's guardian can also select an appropriate image. The cartridge 86 is positioned and the screen 30 is advanced to the selected image by the methods described above. A dolly may be used to transport the cartridge to the room 4. When the selected image is displayed, movement of the screen 30 is stopped. If sounds, music or odors are to be provided, they are initiated, as well.

As the patient enters the MRI room 4, the patient can see the displayed image. The patient can also hear the sounds and smell the odors, if provided. The patient may also see portions of the room 4 including portions of the selected image through the windows 80a, 80b prior to entering the room, if provided. The patient also sees the complementary scenes preferably provided on the MRI assembly. The room 4 does not look like an inhibiting medical procedure room.

The patient is thereby calmed. The patient is positioned on the bed and the bed is adjusted to obtain the appropriate positioning of the patient to conduct the desired MRI procedure, as in a conventional MRI procedure. The MRI procedure can then be performed in an ordinary manner. After completion of the procedure, the patient leaves the room 4. The screen 30 may or may not be moving during the medical procedure. Preferably, the screen is stationary to reduce the risk of patient movement caused by looking at a moving screen.

If the next patient selects a different image, on the same cartridge 86, changing the image of the screen 30 is easily accomplished by moving the screen out of or into the cartridge 86, as discussed above. If the desired image is not on the current cartridge 86, the current cartridge can be easily changed with one that contains the desired image. The current cartridge 86 is removed from the pillow block 52 and the bearing 88 and the replacement delivery cartridge 86 is easily slid into place.

Figure 12:
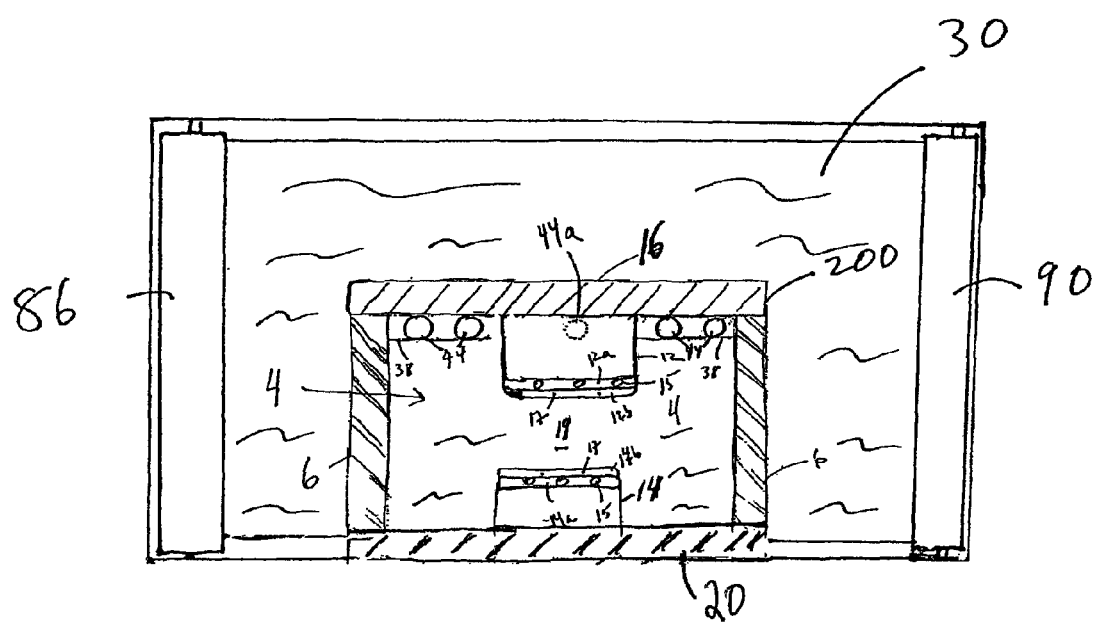
FIG. 12 is a front view of an MRI room in accordance with another embodiment of the invention, wherein an MRI assembly is within the room.

While in the above description, the room 4 is defined by an open MRI assembly 10, the room 4 may be a conventional MRI room containing an open MRI assembly 200, as shown in FIG. 12. The MRI assembly 200 may include the same components as the MRI assembly 10 and those components are commonly numbered.

Other types of MRI assemblies known in the art may be provided in the room, as well. For example, the MRI assembly may be an upright assembly for imaging a patient in a standing position, as disclosed in U.S. Pat. No. 6,075,364, assigned to the assignee of the present invention and incorporated by reference herein, in its entirety, for example. Such an MRI assembly is situated within the MRI room. The poles 6 of the magnet assembly create a magnetic field extending across the gap in a horizontal orientation, instead of a vertical orientation, as in the MRI assembly 10 of FIG. 1A and FIG. 1B. The patient is situated within the gap between the poles (and associated hardware, if any), facing out of the gap. The patient can thereby see at least portions of the screen 30 during a procedure.

The present invention may also be useful to calm a patient undergoing an MRI procedure in a superconducting MRI assembly. In certain assemblies and in certain procedures, the patient's head extends out of the gap or bore of the superconducting magnet. The patient can then see at least part of the image. In other cases, where the patient's head is within the bore of superconducting magnet, the bore may include a reflective mirror or the patient may be provided with glasses with reflecting surfaces, as described in U.S. Pat. No. 5,076,275, so that the patient can see out of the bore. The patient can then see the image on the screen 30 and be calmed. The patient may also be calmed by the image, the other decorations, the sounds and the odors that may be provided in the room in accordance with the present invention, as the patient enters the room.

The present invention may also be useful with other types of medical procedures. For example, the present invention may be useful with other imaging procedures, such as computer aided tomography (CAT) scans. The present invention may also be useful to calm a patient during examining, exploratory and surgical procedures.

It should be understood that the above description is only representative of illustrative examples of embodiments and implementations. Modifications and variations to the illustrated embodiments may be made without going beyond the scope of the present invention, which is defined by the following claims.

What is claimed is:

1. A room for use in conducting medical procedures, comprising:
a magnetic resonance imaging assembly comprising first and second opposed ferromagnetic elements, first and second ferromagnetic pole supports connected to the first and second ferromagnetic elements and first and second poles supported by the first and second pole supports, respectively;
a floor and a ceiling between the first and second opposed ferromagnetic pole supports; and
a screen disposed, at least in part, within a volume between the first and second pole supports, the screen extending a distance from proximate the first ferromagnetic element to proximate the second ferromagnetic element;
at least one storage means for storing at least a portion of the screen;
wherein a plurality of separate scenes are provided serially on the screen, at least some of the plurality of scenes extending the distance from proximate the first ferromagnetic element to proximate the second ferromagnetic element;
the room further comprising:
means for changing a scene for display by moving the screen out of the storage means and at least partially across the room sufficiently to display a new scene.

2. The room of claim 1, wherein the scene changing means includes means for moving the screen to display a different scene.

3. The room of claim 2, further comprising a switch for controlling the movement of the screen.

4. The room of claim 1, further comprising a cartridge for containing the screen.

5. The room of claim 4, further comprising means for changing the cartridge.

6. The room of claim 1, wherein the screen is arcuate.

7. The room of claim 6, wherein a ceiling of the room further comprises lighting disposed proximate to the ceiling.

8. The room of claim 1, wherein the first and second poles are decorated to correspond to an image on the screen.

9. The room of claim 1, further comprising an acoustic means for providing sounds.

10. The room of claim 1, further comprising a scent means for providing smells.

11. The room of claim 1, further comprising illumination behind the screen.

12. The room of claim 1, wherein each scene comprises at least one image.

13. The room of claim 1, wherein the screen is supported, at least in part, by the ceiling.

14. The room of claim 1, wherein:
at least some of the plurality of scenes have a common theme;
the room further comprising:
a first decoration on the ceiling consistent with the common theme;
a second decoration on the floor consistent with the common theme; and a third decoration on the first and second poles consistent with the common theme.

15. A room for use in conducting medical procedures, comprising:
a floor, a ceiling, and at least one wall between the floor and the ceiling;
a magnetic resonance imaging assembly at least partially within the room, the magnetic resonance imaging assembly comprising first and second opposed ferromagnetic elements, first and second ferromagnetic pole supports connected to the first and second ferromagnetic elements and first and second poles supported by the first and second pole supports, respectively;
a screen disposed, at least in part, within a volume between the first and second pole supports;
a plurality of images on the screen;
a track extending across at least a portion of the room, the track defining a groove extending across at least a portion of the length of the track, to receive a portion of the screen; and
a belt attachable to the portion of the screen, the belt being movable at least in part within the groove for moving the portion of the screen through the groove, to move the screen across the room to display a selected one of the plurality of images.

16. The room of claim 15, wherein the screen further comprises first and second sides, each side comprising at least one image for display in the room.

17. The room of claim 15, wherein the belt comprises means for attaching the portion of the screen to the belt.

18. The room of claim 17, wherein the attachment means enables separation of the screen and the belt.

19. The room of claim 17, further comprising a pulley system and motor for moving the belt through the groove.

20. The room of claim 15, wherein the track is arcuate.

21. The room of claim 15, further comprising a window positioned to enable viewing of an image on the screen from a location exterior of the room.

22. The room of claim 15, further comprising:
a delivery cartridge; and
a take-up cartridge;
wherein the screen is stored wound within the delivery cartridge and is moveable by the moving means to the take-up cartridge to be wound within the take-up cartridge during display of an image.

23. The room of claim 15, further comprising:
a delivery cartridge; and
a roller;
wherein the screen has first and second sides and an image on each side,
the screen is stored wound within the delivery cartridge,
the screen is moveable to the roller to display an image on the first side, and
the screen is moveable around the roller, in front of the first side, to display an image on the second side.

24. The room of claim 15, wherein:
the means for moving moves the screen through the track in a first direction;
the track further defines a second groove extending across at least a portion of the length of the track, to receive a portion of the screen; and
the means for moving moves the screen through the second groove in a second direction different from the first direction.

25. The room of claim 15, wherein:
at least some of the plurality of scenes have a common theme;
the room further comprising:
a first decoration on the ceiling consistent with the common theme;
a second decoration on the floor consistent with the common theme; and
a third decoration on the first and second poles consistent with the common theme.

26. The room of claim 15, wherein the track is attached to at least the ceiling of the room.

27. A room for use in conducting medical procedures, comprising:
a magnetic resonance imaging assembly at least partially within the room, the magnetic resonance imaging assembly comprising first and second opposed ferromagnetic elements, first and second ferromagnetic pole supports connected to the first and second ferromagnetic elements and first and second poles supported by the first and second pole supports, respectively;
a screen disposed, at least in part, within a volume between the first and second pole supports,
hook and loop material on a portion of the screen;
at least one image on the screen;
a track extending across the room;
a belt movably disposed within the track;
hook and loop material on at least a portion of the belt;
a motor coupled to the belt to cause movement of the belt within the track, across the room; and
at least one cartridge to store at least a portion of the screen:
the screen being removably attachable to the belt by mating the hook and loop material on the screen and the belt;
wherein movement of the belt when the screen is removably attached to the belt causes removal of a remaining portion of the screen from the at least one cartridge, movement of the screen along the track to display an image in the room, and entry of a previously displayed portion of the screen into the at least one cartridge; and
the track and the belt are configured to compress the hook and loop material on the screen against the hook and loop material on the belt to removably attach the remaining portion of the screen to the belt as the belt draws the screen into the track and to remove the previously displayed portion of the screen from the belt prior to entry of the previously displayed portion of the screen into the at least one cartridge.

28. The room of claim 27, further comprising a serrated gear coupled to the motor, wherein the belt has a serrated portion for engaging the serrated gear, and the hook and loop material on the screen and the hook and loop material on the belt are compressed between a portion of the belt engaged by the serrated gear and the track to removably attach the remaining portion of the screen to the belt.

29. The room of claim 28, further comprising:
at least one pulley; and
a torque converter;
the pulley comprising the serrated gear, the pulley being connected to the motor and to the torque converter for selectively controlling a speed of movement of the belt along the track.

30. The room of claim 27, wherein the track is arcuate.

31. The room of claim 27, further comprising:
a first strip comprising the hook and loop material on the belt; and
a second strip comprising the mating hook and loop material on the screen;
wherein the belt is attachable to the screen by mating the first and second strips.

32. The room of claim 27, wherein movement of the belt causes movement of the screen out of the cartridge, along the track.

33. The room of claim 32, wherein selective movement of the belt causes selective movement of the screen out of or into the cartridge.

34. The room of claim 27, further comprising:
a ceiling; and
illumination above the ceiling.

35. The room of claim 27, further comprising illumination behind the screen.

36. The room of claim 27, further comprising:
track defines a groove;
the belt is movable within the groove; and
the screen is moved by the belt within the groove.

37. A method of using a room for a medical procedure, comprising:
positioning a patient in a magnetic resonance imaging assembly in a room, the magnetic resonance imaging assembly comprising first and second opposed ferromagnetic elements, first and second ferromagnetic pole supports connected to the first and second ferromagnetic elements and first and second poles supported by the first and second pole supports, respectively;
removably attaching a portion of a screen to a belt at least partially within a volume between the first and second pole supports, the screen comprising a plurality of scenes, each scene comprising at least one image;
moving the belt to move at least a portion of the screen through the volume, to display a selected one of the scenes in the room;
removably attaching remaining portions of the screen to the belt as the belt moves at least a portion of the screen through the volume; and
performing the medical procedure.

38. The method of claim 37, comprising moving the screen to a selected image.

39. The method of claim 37, wherein the moving is performed prior to the positioning.

40. The method of claim 37, further comprising moving the screen to display a second image.

41. The method of claim 40, further comprising:
positioning a second patient with respect to the assembly after moving the screen to display the second image; and
performing a medical procedure on the second patent.

42. The method of claim 40, wherein the screen is stored in a cartridge and the second selected image is displayed by replacing a first cartridge by a second cartridge and advancing the screen from the second cartridge to display the second selected image.

43. The method of claim 37, further comprising providing sounds in the room.

44. The method of claim 37, further comprising providing odors in the room.

45. The method of claim 37, comprising moving the screen along an arcuate track.

46. The method of claim 37, further comprising providing moving images on the displayed image.

47. The method of claim 37, wherein the image is selected by the patient.

48. The method of claim 37, further comprising illuminating a ceiling of the room.

49. The method of claim 37, further comprising illuminating the screen.

50. The method of claim 37, comprising:
moving the belt and a portion of the screen within a groove defined by a track.

51. The method of claim 37, wherein the medical procedure is a magnetic resonance imaging procedure.

52. A room for conducting a magnetic resonance imaging procedure, the room comprising:
an upper ferromagnetic pole support, the upper ferromagnetic pole support defining, at least in part, a ceiling of the room;
a lower ferromagnetic pole support opposing the upper ferromagnetic pole support, the lower ferromagnetic pole support defining, at least in part, a floor of the room;
first and second opposed ferromagnetic plates between the upper and lower ferromagnetic pole supports, the first and second plates defining, at least in part, opposing walls of the room;
first and second opposed ferromagnetic poles supported by the upper and lower ferromagnetic pole supports, respectively, the first and second opposed ferromagnetic poles defining an imaging volume there between;
an arcuate track coupled to the ceiling, the arcuate track extending at least partially around the room, between the imaging volume and at least the first and second walls;
a flexible screen movably supported along the track, wherein the screen extends vertically from the ceiling to the floor;
at least one storage device to store at least a portion of the screen;
the screen having a selectively displayed portion extending at least partially around the room, between the imaging volume and at least the first and second walls, and a selectively stored portion, during use, the selectively stored portion being stored in the at least one storage device; and
a plurality of images on the screen, each image extending from the floor to the ceiling and extending across the displayed portion of the screen, such that the image displayed on the displayed portion of the screen is arcuate;
wherein at least some of the images have a common theme;
the room further comprising:
a first decoration on the ceiling consistent with the common theme;
a second decoration on the floor consistent with the common theme;
a third decoration on the first and second poles consistent with the common theme; and
means for moving the screen along the arcuate track, to selectively display an image.

53. The room of claim 52, wherein the moving means comprises at least one pulley and a motor coupled to the pulley.

54. The room of claim 53, wherein the belt is attached to the pulley, the room further comprising:
attachment means for attaching the belt to the screen.

55. The room of claim 54, wherein the track guides the belt across the room.

56. The room of claim 55, wherein the attachment means comprises at least one of a pair of strips comprising a hook and loop material, a hook, a loop, an adhesive, a snap fit, a button, a zipper, a knot, a hinge, a fastener, a bolt, a cable, a clamp, a dowel, a latch, a pin, a seam, a rivet, a screw or a nail.

57. The room of claim 54, wherein the attachment means is removably attachable.

* * * * *